United States Patent
Kaneko et al.

(10) Patent No.: US 10,959,657 B2
(45) Date of Patent: Mar. 30, 2021

(54) STRESS MANAGEMENT SYSTEM AND STRESS MANAGEMENT METHOD

(71) Applicant: Panasonic Intellectual Property Management Co., Ltd., Osaka (JP)

(72) Inventors: Yuumi Kaneko, Kanagawa (JP); Atsushi Saso, Kanagawa (JP); Naomi Tomiyama, Kyoto (JP); Takamichi Matsusako, Tokyo (JP); Mikiko Matsuo, Nara (JP); Yuichi Aoki, Osaka (JP); Motoji Ohmori, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 692 days.

(21) Appl. No.: 15/700,315

(22) Filed: Sep. 11, 2017

(65) Prior Publication Data

US 2018/0078188 A1 Mar. 22, 2018

(51) Int. Cl.
| | | |
|---|---|---|
| *G01N 33/48* | (2006.01) |
| *A61B 5/16* | (2006.01) |
| *A61B 5/0205* | (2006.01) |
| *A61B 5/024* | (2006.01) |
| *A61B 5/00* | (2006.01) |
| *A61B 5/0531* | (2021.01) |

(52) U.S. Cl.
CPC ............ *A61B 5/165* (2013.01); *A61B 5/0024* (2013.01); *A61B 5/0205* (2013.01); *A61B 5/02438* (2013.01); *A61B 5/746* (2013.01); *A61B 5/0531* (2013.01); *A61B 5/486* (2013.01)

(58) Field of Classification Search
None
See application file for complete search history.

(56) References Cited

U.S. PATENT DOCUMENTS

| | | | |
|---|---|---|---|
| 2001/0049471 A1 | 12/2001 | Suzuki et al. | |
| 2014/0172467 A1* | 6/2014 | He | B60K 28/06 705/4 |
| 2016/0261147 A1* | 9/2016 | Blum | H02J 50/80 |
| 2017/0090561 A1* | 3/2017 | Dow | G06F 3/013 |
| 2017/0173394 A1* | 6/2017 | Rider | A63B 24/0075 |

FOREIGN PATENT DOCUMENTS

| | | |
|---|---|---|
| JP | 2001-344352 | 12/2001 |
| JP | 2012-249797 | 12/2012 |
| JP | 2016-115057 | 6/2016 |
| JP | 2016-147006 | 8/2016 |

* cited by examiner

*Primary Examiner* — Anna Skibinsky
(74) *Attorney, Agent, or Firm* — Greenblum & Bernstein, P.L.C.

(57) ABSTRACT

A stress management system comprises: a first sensor that detects biological data of a user; a second sensor that detects life log data indicating an action history of the user; a generator that generates stress data using the biological data, the stress data indicating a time series variation of a stress level of the user; an estimator that, when the stress level of the user included in the stress data exceeds a first threshold, estimates whether or not stress of the user is interpersonal stress caused by contact with another person, using the life log data; and a notifier that notifies the user of a result of the estimation by the estimator and notifies a notification target person different from the user of notification content based on the result of the estimation by the estimator.

13 Claims, 16 Drawing Sheets

| USER ID | DATE | TIME | BIOLOGICAL DATA |
|---|---|---|---|
| A | AUGUST 2, 2016 | 10:30 | HEART RATE Ba11, BODY TEMPERATURE Ba12, BLOOD PRESSURE Ba13, PERSPIRATION Ba14 |
| B | AUGUST 2, 2016 | 10:31 | HEART RATE Ba21, BODY TEMPERATURE Ba22, BLOOD PRESSURE Ba23, PERSPIRATION Ba24 |
| A | AUGUST 2, 2016 | 11:30 | HEART RATE Ba31, BODY TEMPERATURE Ba32, BLOOD PRESSURE Ba33, PERSPIRATION Ba34 |
| B | AUGUST 2, 2016 | 11:31 | HEART RATE Ba41, BODY TEMPERATURE Ba42, BLOOD PRESSURE Ba43, PERSPIRATION Ba44 |

| USER ID | DATE | TIME PERIOD | LIFE LOG DATA |
|---|---|---|---|
| A | AUGUST 2, 2016 | 10:00 - 12:00 | SOUND DATA A1 |
| B | AUGUST 2, 2016 | 11:00 - 13:00 | SOUND DATA A2 |
| A | AUGUST 2, 2016 | 12:00 - 15:00 | SOUND DATA A3 |
| C, D | AUGUST 2, 2016 | 16:00 - 17:00 | SOUND DATA A4 |
| ... | ... | ... | ... |

FIG. 9

| TYPE | TERM |
|---|---|
| POWER HARASSMENT | INCOMPETENT |
| | GOLDBRICKER |
| | YOU ARE FIRED |
| | WHY CAN'T YOU DO SUCH EASY THING? |
| | SON IS KNOWN BY HIS FATHER |
| | ... |
| SEXUAL HARASSMENT | SHALL WE GO TO MEAL? |
| | SHALL WE GO OUT FOR PLAY? |
| | I LIKE YOU |
| | PLEASE STOP DOING IT |
| | I WILL SCREAM |
| | ... |

FIG. 10

| USER ID | SCHEDULE DATA | | |
|---|---|---|---|
| | DATE | TIME PERIOD | ACTION CONTENT |
| A | AUGUST 2, 2016 | 10:00 - 12:00 | BUSINESS TRIP |
| A | AUGUST 3, 2016 | 13:00 - 15:00 | MEETING |
| B | AUGUST 6, 2016 | 13:00 - 16:00 | BASEBALL |
| A | AUGUST 7, 2016 | 6:30 - 17:00 | GOLF |
| C | AUGUST 7, 2016 | 13:00 - 17:00 | SOCCER |

FIG. 11

| TYPE | ACTION CONTENT |
|---|---|
| TASK | BUSINESS TRIP |
| | MEETING |
| | PAPERWORK |
| | ... |
| SPORTS | GOLF |
| | BASEBALL |
| | SOCCER |
| | ... |
| ... | ... |

FIG. 12

| TYPE | DETAILED TYPE | TECHNICAL TERM |
|---|---|---|
| TASK | NEGOTIATION | TRANSACTION, BREAKDOWN, ... |
| | CONTRACT | COMPLIANCE, ... |
| | CONFERENCE | PROGRESS, MINUTES, AGENDA, ... |
| | ... | ... |
| SPORTS | GOLF | BOGIE, DOUBLE BOGIE, ... |
| | BASEBALL | HIT, HOME RUN, DOUBLE PLAY, ... |
| | SOCCER | GOAL, OFFSIDE, ... |
| | ... | ... |
| ... | ... | ... |

FIG. 13

| TYPE | GENERAL TERM |
|---|---|
| GOLF | DOUBLE BOGIE |
|  | ... |
| BASEBALL | HANSHIN |
|  | ... |
| SOCCER | GAMBA |
|  | ... |
| ... | ... |

FIG. 16

| NOTIFICATION DATE | NOTIFICATION TIME | NOTIFICATION HISTORY DATA ||||||| RELAXATION INFORMATION | HUMAN RELATION INFORMATION |
| --- | --- | --- | --- | --- | --- | --- | --- | --- | --- | --- |
| | | TARGET USER ID | DETECTION DATE | DETECTION TIME | TYPE | ASSAILANT ID | NOTIFICATION TARGET PERSON ID | NOTIFICATION TYPE | | |
| JULY 30, 2016 | 0:00 | C | JULY 29, 2016 | 11:00 | POWER HARASSMENT | A | A | ANONYMOUS NOTIFICATION | RELAXED | DETERMINED |
| AUGUST 2, 2016 | 0:00 | A | AUGUST 1, 2016 | 11:00 | BASEBALL | (NONE) | (NONE) | OUTSIDER NOTIFICATION | UN-RELAXED | UNDETERMINED |
| AUGUST 2, 2016 | 0:00 | D | AUGUST 1, 2016 | 14:00 | SEXUAL HARASSMENT | B | B | OUTSIDER NOTIFICATION | UN-RELAXED | UNDETERMINED |
| AUGUST 2, 2016 | 0:00 | D | AUGUST 1, 2016 | 15:00 | SEXUAL HARASSMENT | A | B | VICTIM NAME NOTIFICATION | UN-RELAXED | UNDETERMINED |
| AUGUST 2, 2016 | 0:01 | C | AUGUST 1, 2016 | 16:00 | POWER HARASSMENT | D | E | ANONYMOUS NOTIFICATION | UN-RELAXED | UNDETERMINED |

FIG. 20

| DETERMINATION DATE | USER ID | RELATION INFORMATION |
|---|---|---|
| AUGUST 2, 2016 | D, A | TENSE |
| AUGUST 29, 2016 | X, Y | TENSE |
| ... | ... | ... |

STRESS MANAGEMENT SYSTEM AND STRESS MANAGEMENT METHOD

BACKGROUND

1. Technical Field

The present disclosure relates to a stress management system and a stress management method for managing psychological stress of a user.

2. Description of the Related Art

There has been known a technique for calculating a degree of psychological stress of a user (hereinafter referred to as stress level) using biological data such as a heart rate and a blood pressure and managing the psychological stress of the user using the calculated stress level.

For example, Japanese Unexamined Patent Application Publication No. 2012-249797 (JP2012-249797A) discloses that weighted addition of a heart rate, a body temperature, a blood pressure, and perspiration of an observed person using predetermined coefficients is performed to obtain a stress value of the observed person. JP2012-249797A also discloses that an action performed by the observed person, a stress value of the observed person at the time of the action, and a captured image of the observed person performing the action are stored in time series in association with one another, and then an action and an image of the observed person associated with a stress value that satisfies a predetermined condition, for example, a maximum stress value in one day are displayed.

SUMMARY

One non-limiting and exemplary embodiment provides an improved stress management system that manages psychological stress of a user.

In one general aspect, the techniques disclosed here feature a stress management system, comprising: a first sensor that detects biological data of a user; a second sensor that detects life log data indicating an action history of the user; a generator that generates stress data using the biological data, the stress data indicating a time series variation of a stress level of the user; an estimator that, when the stress level of the user included in the stress data exceeds a first threshold, estimates whether or not stress of the user is interpersonal stress caused by contact with another person, using the life log data; and a notifier that notifies the user of a result of the estimation by the estimator and notifies a notification target person different from the user of notification content based on the result of the estimation by the estimator.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 9 is a diagram illustrating an example of an interpersonal stress term table;

FIG. 10 is a diagram illustrating an example of data stored in a schedule storage;

FIG. 11 is a diagram illustrating an example of a specialty type determination table;

FIG. 12 is a diagram illustrating an example of a technical term table;

FIG. 13 is a diagram illustrating an example of a general term table;

FIG. 16 is a diagram illustrating an example of data stored in a notification history storage;

FIG. 20 is a diagram illustrating an example of data stored in a human map storage.

Figure 1:
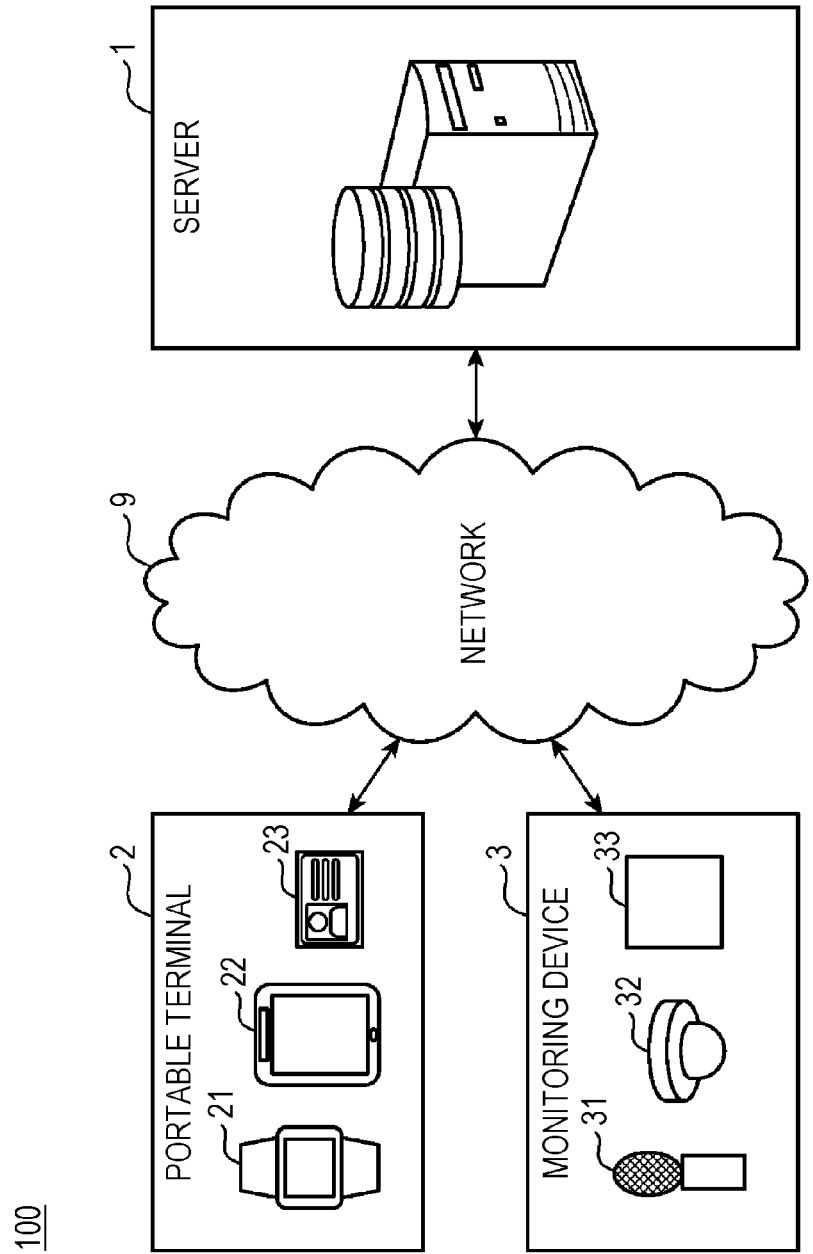
FIG. 1 is a diagram illustrating an entire image of a stress management system according to a first embodiment of the present disclosure.

DETAILED DESCRIPTION (Underlying Knowledge Forming Basis of the Present Disclosure)

In recent years, in companies, there has been a tendency toward an increase in employees leaving jobs because of interpersonal stress, for example, power harassment and sexual harassment, caused by contact with others. In schools, there has been also a tendency toward an increase in students refusing to go to school because of interpersonal stress due to bullying, alienation, and the like.

Meanwhile, in recent years, use of a wearable terminal has enabled measurement of biological data in a noncontact manner. Therefore, it has been becoming easier to grasp a stress level of a user from the biological data than in the past. Further, by using a portable terminal such as a smartphone or a camera and a microphone provided in a meeting room or a classroom, it has been becoming easier to store, as image data and sound data, so-called life log data indicating action histories of an employee or a student.

Therefore, it is conceivable to apply these techniques to the technique disclosed in JP2012-249797A described above to store the stress level of the user grasped from the biological data and the life log data in association with each other. It is conceivable to display an action and an image of the user at the time when the stress level satisfies a condition that the stress level exceeds a predetermined threshold and the user is considered to have some kind of stress.

In this case, the user can be aware of an action that affects an increase in the stress level. However, the user cannot determine whether the stress of the user is stress caused by an emotion of the user such as a tension or an anxiety, or interpersonal stress caused by contact with another person such as a remark or manner of the other person with whom the user had contact during the action. Therefore, although the user has the interpersonal stress, the user is likely to erroneously determine that the user has stress caused by an emotion of the user. Even if the other person having a contact relation with the user visually recognizes the displayed action and the displayed image of the user, the other person cannot determine at all whether the user has the interpersonal stress. As a result, it is likely that the user cannot relax his/her own interpersonal stress and cannot solve the problems.

On the basis of the knowledge, the inventors earnestly examined how to make a user and others having the contact relation with the user aware that the user has the interpersonal stress. As a result, the inventors completed the present disclosure.

That is, in the related art, it is considered that further improvement is necessary to make not only the user but also the others having the contact relation with the user aware that the user has the interpersonal stress caused by contact with the others.

The present disclosure has been devised to solve the problems, and an object of the present disclosure is to provide a stress management system and a stress management method that can make not only a user but also others having a contact relation with the user aware that the user has the interpersonal stress.

An overview of an aspect of the present disclosure is as described below.

[Item 1]
A stress management system, comprising:
a first sensor that detects biological data of a user;
a second sensor that detects life log data indicating an action history of the user;
a generator that generates stress data using the biological data, the stress data indicating a time series variation of a stress level of the user;
an estimator that, when the stress level of the user included in the stress data exceeds a first threshold, estimates whether or not stress of the user is interpersonal stress caused by contact with another person, using the life log data; and
a notifier that notifies the user of a result of the estimation by the estimator and notifies a notification target person different from the user of notification content based on the result of the estimation by the estimator.

With the configuration of the item 1, if the stress level of the user generated using the biological data exceeds the first threshold, it is estimated using, for example, life log data corresponding to a detection time point of biological data affecting an increase in the stress level whether the stress of the user is the interpersonal stress. If it is estimated that the stress of the user is the interpersonal stress, a result of the estimation is notified to the user. Further, notification content concerning the interpersonal stress of the user, which can be determined using the result of the estimation, is notified to a notification target person having a contact relation with the user. Consequently, it is possible to make the user and others having a contact relation with the user aware that the user has the interpersonal stress to a degree of the stress level exceeding the first threshold.

[Item 2]
The stress management system according to the item 1, wherein
when the stress of the user is estimated to be interpersonal stress, the estimator further estimates a type of interpersonal stress and an assailant who is a cause of the stress using the life log data, and
the notifier notifies the assailant that an anonymous victim has the stress classified as the type of interpersonal stress because of the assailant.

With the configuration of the item 2, a result of the estimation of the type of the interpersonal stress of the user and the assailant, who is the cause of the stress, is notified to the user. Consequently, it is possible to further make the user aware contact with which person causes the interpersonal stress of the user and what type of interpersonal stress the interpersonal stress is. As a result, the user can easily take appropriate measures for reducing the interpersonal stress of the user.

With the configuration of the item 2, the assailant, who is the cause of the interpersonal stress, is notified that the victim having the interpersonal stress because of the assailant is present. Consequently, it is possible to make the assailant aware that the assailant needs to refrain from an action that gives the interpersonal stress to others.

[Item 3]
The stress management system according to the item 2, wherein, when the stress level of the user does not fall below the first threshold by a first point in time when a first period elapses from the notification of the notification content to the assailant, the notifier further notifies the assailant that the anonymous victim is the user.

It is assumed that the interpersonal stress of the user is not relaxed to a degree at which the stress level has decreased below the first threshold at the first time point when the first time elapses after it is notified to the assailant that the victim having the interpersonal stress is present. In this case, with the configuration of the item 3, it is further notified to the assailant that the victim is the user.

Consequently, it is possible to make the assailant to aware that the assailant needs to refrain from an action that gives the interpersonal stress to the user.

[Item 4]
The stress management system according to the item 3, wherein, when the stress level of the user does not fall below the first threshold by a second point in time when a second period elapses from the first point in time, the notifier further notifies an outsider previously associated with the assailant that the user has the stress classified as the type of interpersonal stress because of the assailant.

It is assumed that the interpersonal stress of the user is not relaxed to a degree at which the stress level has decreased below the first threshold at the second time point when the second time elapses after it is notified to the assailant that the victim having the interpersonal stress is the user. In this case, with the configuration of the item 4, it is notified to the outsider associated with the assailant in advance that the user has the interpersonal stress because of the assailant.

Consequently, it is possible to make the outsider aware that the outsider needs to advise the assailant that the assailant refrain from an action that gives the interpersonal stress to the user.

[Item 5]

The stress management system according to the item 2, wherein, when a stress level of the assailant exceeds the first threshold at a point in time corresponding to a point in time when the stress level of the user exceeds the first threshold, the notifier further notifies an outsider previously associated with each of the user and the assailant that the user and the assailant are in tense relations.

When the user and the assailant in the tense relations come into contact, the stress levels of the user and the assailant are considered to increase. With the configuration of the item 5, when both of the stress levels of the user and the assailant exceed the first threshold, the outsider associated with each of the user and the assailant in advance is notified that the user and the assailant are in the tense relations. Consequently, it is possible to appropriately determine that the user and the assailant are in the tense relations and make the outsider aware of a result of the determination.

[Item 6]

The stress management system according to the item 2, further comprising a human map storage, wherein when a stress level of the assailant exceeds the first threshold at a point in time corresponding to a point in time when the stress level of the user exceeds the first threshold, the notifier stores, in the human map storage, information indicating that the user and the assailant are in tense relations.

When the user and the assailant in the tense relations come into contact, the stress levels of the user and the assailant are considered to increase. With the configuration of the item 6, when both of the stress levels of the user and the assailant exceed the first threshold, the indication that the user and the assailant are in the tense relations is stored in the human map storage. Consequently, it is possible to appropriately determine that the user and the assailant are in the tense relations and make the user who refers to data stored in the human map storage aware of a result of the determination.

[Item 7]

The stress management system according to the item 1, wherein when the estimator does not estimate that the stress of the user is interpersonal stress, the estimator further estimates a type of the stress using the life log data, and the notifier notifies an outsider previously associated with the user that the user has the stress classified as the type.

With the configuration of the item 7, the type of the stress of the user is notified to the user. Consequently, it is possible to make the user aware what type of stress the stress of the user is. As a result, the user can easily take appropriate measures for reducing the stress of the user.

With the configuration of the item 7, the outsider associated with the user in advance is notified that the user has the stress. Consequently, it is possible to make the outsider aware that the outsider needs to advise the user that the user refrain from an action that causes stress.

[Item 8]

The stress management system according to the item 1, wherein the estimator further estimates a type of the stress of the user using the life log data, and when the stress level of the user even exceeds the first threshold, but does not exceed a second threshold previously associated with the type of the stress, the notifier does not notify the user of the result and does not notify the notification target person of the notification content.

Depending on a type of the stress of the user, it is considered likely that the stress level of the user is increased to the contrary by making the user aware that the user has the stress. However, with the configuration of the item 8, if the stress level of the user even exceeds the first threshold, but does not exceed the second threshold associated with stresses in advance, the result of the estimation and the notification content are not notified.

That is, with the configuration of the item 8, by deciding the second threshold as appropriate according to the type of the stress, it is possible to flexibly change determination on whether to notify the user and the notification target person that the user has the stress. Consequently, it is possible to reduce the likelihood that the user increases the stress level as explained above.

[Item 9]

The stress management system according to the item 2, wherein, when a sum of stress levels satisfying a predetermined condition among stress levels of participants exceeds a second threshold, the notifier further notifies the assailant that the participants are likely to have stress classified as the type of interpersonal stress because of the assailant, action histories of the participants being included in the life log data at a point in time corresponding to a point in time when the stress level of the user exceeds the first threshold, the participants being different from the assailant.

It is assumed that the sum of the stress levels satisfying the predetermined condition among the stress levels of the participants exceeds the second threshold. In this case, it is considered likely that the participants will have an interpersonal stress of the same type as the interpersonal stress of the user while repeating contact with the assailant.

However, with the configuration of the item 9, in such a case, the assailant is notified that at least a part of the participants are likely to have the interpersonal stress of the type same as the interpersonal stress of the user. Consequently, it is possible to make the assailant aware beforehand that the assailant needs to refrain from an action such that the participants do not have the interpersonal stress.

[Item 10]

The stress management system according to the item 1, wherein the second sensor detects, as the life log data, sound data including voice of the user, and when the stress level of the user even exceeds the first threshold but an emotion of the user recognized from the sound data included in the life log data indicates that the user has no stress, the notifier does not notify the user of the result and does not notify the notification target person of the notification content.

When the emotion of the user recognized from the sound data included in the life log data indicates that the user has no stress, the user is considered to have no stress. Therefore, it is considered unnecessary to notify the result of the estimation and the notification content. With the configuration of the item 10, it is possible to avoid unnecessarily performing notification in such a case.

[Item 11]

The stress management system according to the item 1, wherein the second sensor detects, as the life log data, image data including an image of the user, and when the stress level of the user even exceeds the first threshold but an expression of the user recognized from the image data included in the life log data indicates that the user has no stress, the notifier does not notify the user of the result and does not notify the notification target person of the notification content.

When the expression of the user recognized from the image data included in the life log data indicates that the user has no stress, the user is considered to have no stress. Therefore, it is considered unnecessary to notify the result of the estimation and the notification content. With the configuration of the item 11, it is possible to avoid unnecessarily performing notification in such a case.

The present disclosure can be realized not only as the stress management system including the characteristic configurations explained above but also as a stress management method for executing characteristic processing corresponding to the characteristic configurations included in the stress management system. Therefore, it is possible to achieve, with other aspects explained below, the same effects as the effects of the stress management system.

[Item 12]

A stress management method, comprising:
detecting biological data of a user;
detecting life log data indicating an action history of the user;
generating stress data using the biological data, the stress data indicating a time series variation of a stress level of the user;
estimating whether or not stress of the user is interpersonal stress caused by contact with another person, using the life log data, when the stress level of the user included in the stress data exceeds a first threshold; and
notifying the user of a result of the estimation and notifying a notification target person different from the user of notification content based on the result of the estimation.

The present disclosure may be realized as a computer program for causing a computer to execute the characteristic processing included in the stress management method. It goes without saying that the computer program can be distributed via a computer-readable nontransitory recording medium such as a CD-ROM or a communication network such as the Internet.

Note that all of embodiments explained below indicate specific examples of the present disclosure. Numerical values, shapes, components, steps, the order of the steps, and the like described in the following embodiments are examples and are not meant to limit the present disclosure. Among the components in the following embodiments, components not described in independent claims indicating a most significant concept are explained as optional components. In all of the embodiments, respective contents can be combined.

First Embodiment (Overview of a System)

Embodiments of the present disclosure are explained below with reference to the drawings. FIG. 1 is a diagram illustrating an overview of a stress management system according to a first embodiment of the present disclosure. As illustrated in FIG. 1, a stress management system 100 includes a portable terminal 2 carried by a user, a monitoring device 3 set in a predetermined room such as a meeting room or a classroom, a network 9 such as a LAN (Local Area Network) or the Internet, and a server 1.

The portable terminal 2 includes a wearable terminal 21, a smartphone 22, and an individual identification card 23.

The wearable terminal 21 and the smartphone 22 respectively include biometric sensors, nonvolatile memories, and wireless communication circuits. The biometric sensors detect biological data such as a heart rate, a body temperature, a blood pressure, and perspiration of a user. For example, identification information of the user (hereinafter referred to as user ID) is stored in the nonvolatile memories.

The wireless communication circuit of the wearable terminal 21 transmits the biological data detected by the biometric sensor and the user ID stored in the nonvolatile memory to the smartphone 22 through wireless communication. Note that the wireless communication circuit of the wearable terminal 21 may transmit the biological data and the user ID to the server 1 via the network 9 through wireless communication.

The wireless communication circuit of the smartphone 22 transmits the biological data and the user ID received from the wearable terminal 21 to the server 1 via the network 9 through wireless communication. The wireless communication circuit of the smartphone 22 transmits the biological data detected by the biometric sensor of the smartphone 22 and the user ID stored in the nonvolatile memory of the smartphone 22 to the server 1 via the network 9 through wireless communication.

The smartphone 22 further includes a microphone that collects sound around the smartphone 22 and a camera that photographs an image around the smartphone 22. The wireless communication circuit of the smartphone 22 transmits sound data indicating the sound collected by the microphone, image data indicating the image photographed by the camera, the user ID stored in the nonvolatile memory, and a date and a time period when the sound collection and the photographing are performed to the server 1 via the network 9.

The individual identification card 23 is a so-called IC card incorporating an IC (Integrated Circuit) chip. A profile, which is a characteristic of the user, is printed on the surface of the individual identification card 23. The profile of the user includes, for example, a user ID, an image indicating the face of the user, a name, and a department to which the user belongs. A memory chip and a wireless communication circuit are incorporated in the individual identification card 23. For example, data indicating the profile of the user (hereinafter referred to as profile data) is stored in the memory chip. The wireless communication circuit performs wireless communication when the individual identification card 23 approaches a card reader 33 or when the individual identification card 23 comes into contact with the card reader 33. For example, the wireless communication circuit transmits the profile data stored in the memory chip to the card reader 33. The card reader 33 is explained below.

Note that the wireless communication circuit of the individual identification card 23 may transmit the profile data stored in the memory chip to the server 1 via the network 9 through wireless communication. A biometric sensor that detects biological data may be provided in the individual identification card 23. Accordingly, the wireless communication circuit of the individual identification card 23 may transmit the biological data detected by the biological data to the card reader 33. The wireless communication circuit of the individual identification card 23 may transmit the biological data detected by the biometric sensor to the server 1 via the network 9.

The monitoring device 3 includes, for example, a sound collection microphone 31, a monitoring camera 32, and the card reader 33.

The sound collection microphone 31 collects sound in a room in which the sound collection microphone 31 is set and transmits sound data indicating the collected sound and a date and a time period when the sound collection is performed to the server 1 via the network 9.

The monitoring camera 32 photographs an image of an entire room in which the monitoring camera 32 is set and transmits image data indicating the photographed image and a date and a time period when the photographing is performed to the server 1 via the network 9.

The card reader 33 is set, for example, near a door of a room in which the card reader 33 is set. For example, when the user enters a room, the card reader 33 performs wireless communication with the wireless communication circuit in the individual identification card 23 carried by the user when the individual identification card 23 approaches the card reader 33 or when the individual identification card 23 is brought into contact with the card reader 33. The card reader 33 acquires the profile data stored in the memory chip in the individual identification card 23 through wireless communication. The card reader 33 transmits predetermined information, for example, the user ID included in the acquired profile data to the server 1 via the network 9.

The server 1 receives, via the network 9, the data transmitted from the portable terminal 2 and the monitoring device 3 and executes predetermined processing using the received data. Details of the processing executed by the server 1 are explained below.

(Functional Configuration)

Figure 2:
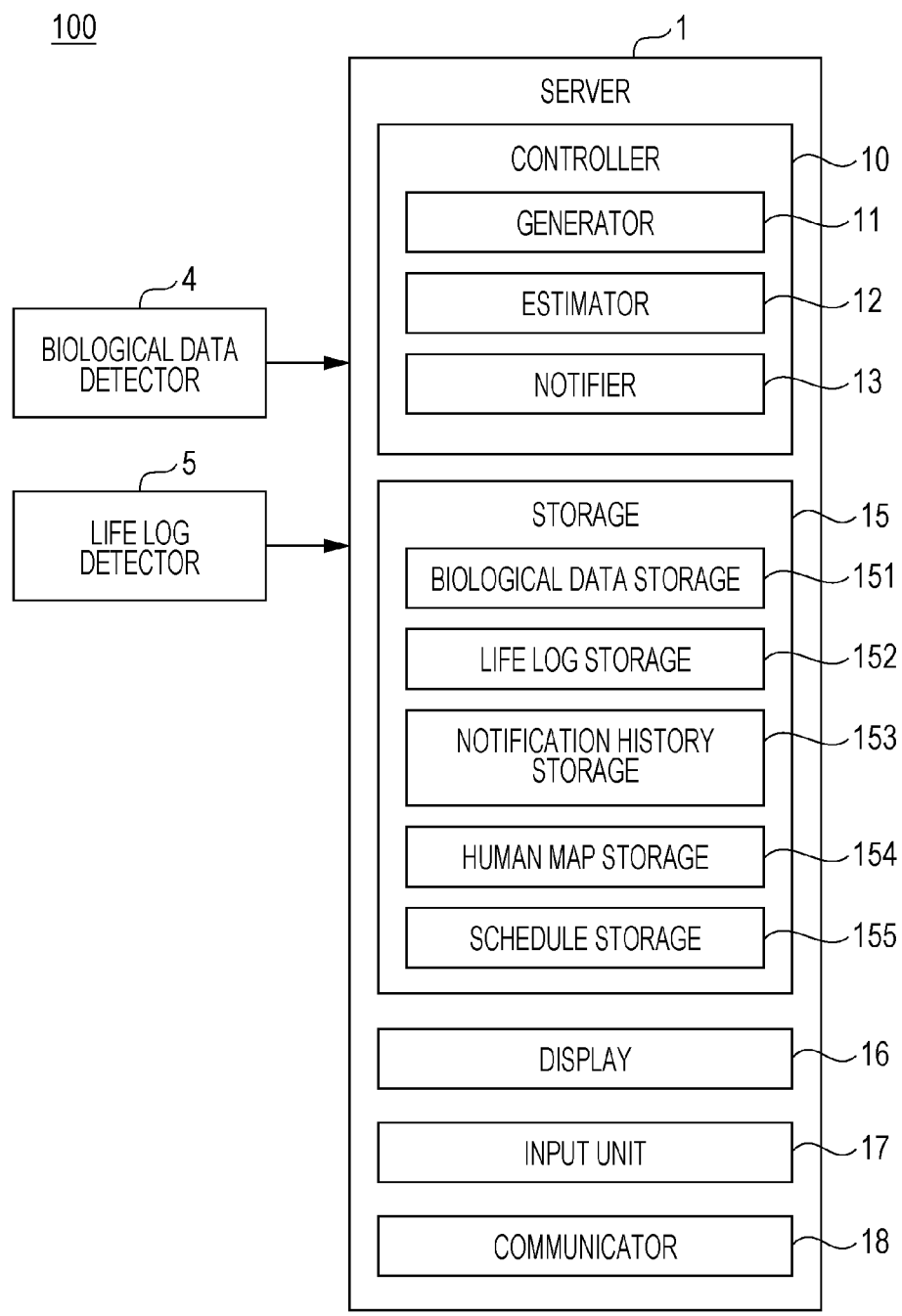
FIG. 2 is a block diagram illustrating an example of a functional configuration of the stress management system according to the first embodiment of the present disclosure.

A functional configuration of the stress management system 100 according to the first embodiment of the present disclosure is explained. FIG. 2 is a block diagram illustrating an example of the functional configuration of the stress management system 100 according to the first embodiment of the present disclosure. The stress management system 100 functions as a biological data detector 4, a life log detector 5, and the server 1. The biological data detector 4 is an example of a first sensor. The life log detector 5 is an example of a second sensor The biological data detector 4 is configured by the wearable terminal 21 and the smartphone 22 illustrated in FIG. 1. The biological data detector 4 detects biological data of the user with the biometric sensors included in the wearable terminal 21 and the smartphone 22. The biological data detector 4 transmits the detected biological data and the user ID stored in the nonvolatile memories of the wearable terminal 21 and the smartphone 22 to the server 1 via the network 9.

The life log detector 5 is configured by the smartphone 22, the individual identification card 23, and the monitoring device 3 illustrated in FIG. 1. The life log detector 5 detects life log data indicating an action history of the user and transmits the detected life log data, the user ID, and a date and a time period when an action of the user is performed to the server 1 via the network 9.

Specifically, when the user is performing an action such as eating out, the life log detector 5 detects, as life log data, sound data indicating conversation collected by the microphone included in the smartphone 22 and image data indicating a state of the action photographed by the camera included in the smartphone 22. The life log detector 5 transmits the life log data, the user ID stored in the nonvolatile memory included in the smartphone 22, and a date and a time period when the sound collection and the photographing are performed to the server 1.

When the user is conducting, for example, a conference in a room in which the monitoring device 3 is set, the life log detector 5 detects, as life log data, sound data indicating conversation collected by the sound collection microphone 31 and image data indicating a state of an action photographed by the monitoring camera 32. The life log detector 5 transmits the life log data, user IDs of all users included in profile data read out by the card reader 33 from the individual identification cards 23 of all the users acting in the room, and a date and a time period when the sound collection and the photographing are performed to the server 1.

The server 1 functions as a controller 10, a storage 15, a display 16, an input unit 17, and a communicator 18.

The controller 10 is configured by a microcomputer including a CPU (Central Processing Unit), a volatile memory such as a RAM (Random Access Memory), and a nonvolatile memory such as an EEPROM (Electrically Erasable Programmable Read-Only Memory). The controller 10 controls the operations of units of the server 1 by causing the CPU to execute a control program stored in the nonvolatile memory. The controller 10 operates as a generator 11, an estimator 12, and a notifier 13. Details of the generator 11, the estimator 12, and the notifier 13 are explained below.

The storage 15 is configured by a storage device such as a HDD (Hard Disk Drive) or a SSD (Solid State Drive). A storage region included in the storage 15 is used as a biological data storage 151, a life log storage 152, a notification history storage 153, a human map storage 154, and a schedule storage 155. Details of the biological data storage 151, the life log storage 152, the notification history storage 153, the human map storage 154, and the schedule storage 155 are explained below.

The display 16 is configured by, for example, a liquid crystal display and displays a result of processing performed by the controller 10. Note that the display 16 may be configured by a display device of a tablet terminal communicatively connected to the server 1 via the network 9 illustrated in FIG. 1.

The input unit 17 includes, for example, a touch panel or hardware buttons and receives input of instructions and information from the user to the server 1.

The communicator 18 is configured by various communication interface circuits for the server 1 to communicate with an external apparatus via the network 9. The external apparatus includes the portable terminal 2, the monitoring device 3, and external servers not illustrated in the figure such as a mail server and a Web server.

(Biological Data Storage Processing)

Figures 3, 4:
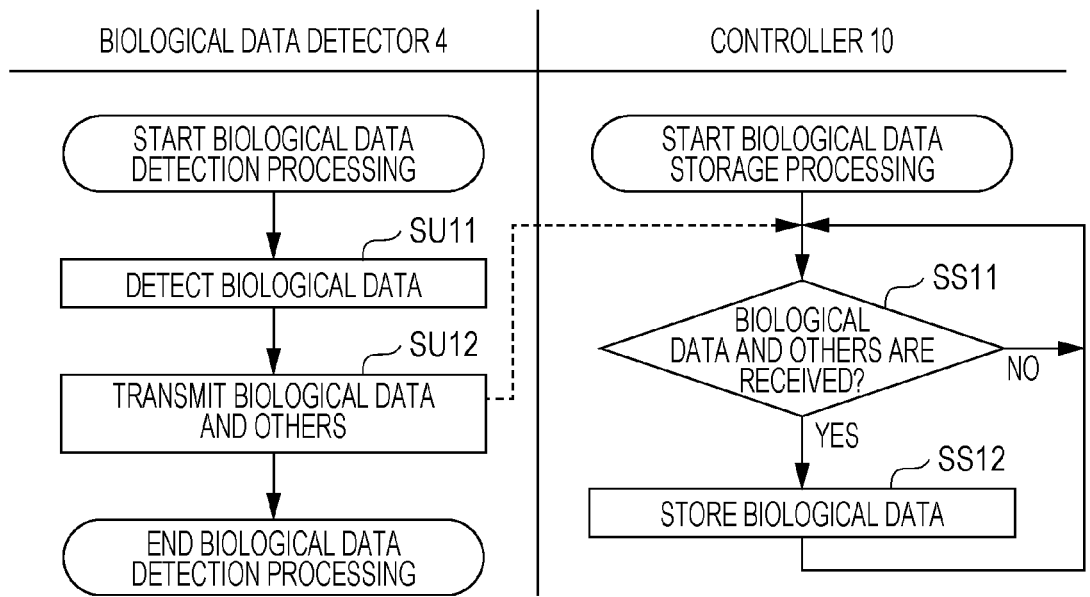
FIG. 3 is a flowchart for explaining the operations of biometric-data detection processing and biometric-data storage processing.
FIG. 4 is a diagram illustrating an example of data stored in a biological data storage.

The operation of the stress management system 100 is explained below. The biological data detector 4 executes, periodically, for example, in every one hour, biological data detection processing for detecting biological data of the user. On the other hand, in the server 1, the controller 10 executes biological data storage processing. The biological data storage processing is processing for storing the biological data detected in the biological data detection processing in the biological data storage 151 in time series. FIG. 3 is a flowchart for explaining the operations of the biological data detection processing and the biological data storage processing. FIG. 4 is a diagram illustrating an example of data stored in the biological data storage 151.

Specifically, as illustrated in FIG. 3, when starting the biological data detection processing, the biological data detector 4 detects biological data of the user (SU11). The biological data detector 4 transmits the biological data detected in SU11 and the user ID to the server 1 (SU12). In this embodiment, in SU11, the biological data detector 4 detects a heart rate, a body temperature, a blood pressure, and perspiration as the biological data. Note that the biological data detector 4 may detect not only these four items but also other items such as a pulse as the biological data.

On the other hand, after the start of the server 1, the controller 10 starts the biological data storage processing. Thereafter, the biological data and the user ID transmitted by the biological data detector 4 are received by the communicator 18 (YES in SS11). When the biological data and the user ID are received by the communicator 18, as illustrated in FIG. 4, the controller 10 stores the user ID (e.g., "A"), a date (e.g., "Aug. 2, 2016") and time (e.g., "10:30") when the biological data and the user ID are received, and the biological data (e.g., "a heart rate Ba11, a body temperature Ba12, a blood pressure Ba13, and perspiration Ba14") in the biological data storage 151 in association with one another (SS12). The controller 10 returns the processing to SS11. Thereafter, the processing in SS11 and subsequent steps is performed.

When the biological data and the user ID transmitted by the biological data detector 4 are not received by the communicator 18 (NO in SS11), the controller 10 returns the processing to SS11. Thereafter, the processing in SS11 and subsequent steps is performed.

(Life Log Data Storage Processing)

Figures 5, 6:
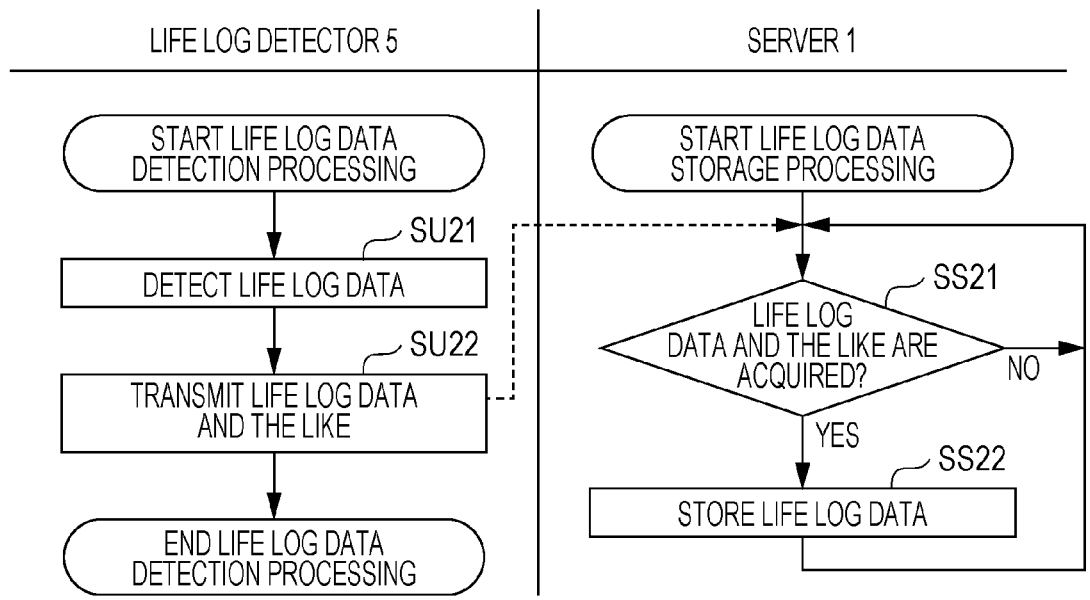
FIG. 5 is a flowchart for explaining the operations of life-log-data detection processing and life-log-data storage processing.
FIG. 6 is a diagram illustrating an example of data stored in a life log storage.

At timing when the user ends an action, the life log detector 5 executes life log data detection processing for detecting life log data of the user. On the other hand, in the server 1, the controller 10 executes life log data storage processing. The life log data storage processing is processing for storing the life log data detected in the life log data detection processing in the life log storage 152. FIG. 5 is a flowchart for explaining the operations of the life log data detection processing and the life log data storage processing. FIG. 6 is a diagram illustrating an example of data stored in the life log storage 152.

Specifically, as illustrated in FIG. 5, when starting the life log data detection processing, the life log detector 5 detects life log data of the user (SU21). In this embodiment, in SU21, the life log detector 5 detects, as the life log data, sound data indicating sound at the time when the user is acting. The life log detector 5 transmits the detected life log data, the user ID, and a date and a time period when the sound is collected to the server 1 (SU22).

On the other hand, after the start of the server 1, the controller 10 starts the life log data storage processing. Thereafter, the life log data, the user ID, and the date and the time period transmitted by the life log detector 5 are received by the communicator 18 (YES in SS21). When the life log data, the user ID, and the date and the time period are received by the communicator 18, as illustrated in FIG. 6, the controller 10 stores the user ID, the date and the time period, and the life log data in the life log storage 152 in association with one another (SS22). The controller 10 returns the processing to SS21. Thereafter, the processing in SS21 and subsequent steps is performed.

For example, data in a first row in FIG. 6 indicates data stored in SS22 when life log data "sound data A1" detected by the microphone of the smartphone 22 carried by a user identified by a user ID "A", the user ID "A", and a date "Aug. 2, 2016" and a time period "10:00 to 12:00" when sound is collected by the microphone are transmitted in SU22.

Data in a fourth row in FIG. 6 indicates data stored in SS22 when life log data "sound data A4" detected by the sound collection microphone 31, user IDs "C and D" read out from the individual identification cards 23 carried by a user identified by the user ID "C" and a user identified by the user ID "D", and a date "Aug. 2, 2016" and a time period "16:00 to 17:00" when sound is collected by the sound collection microphone 31 are transmitted in SU22.

(Stress Estimation Processing)

Figure 7:
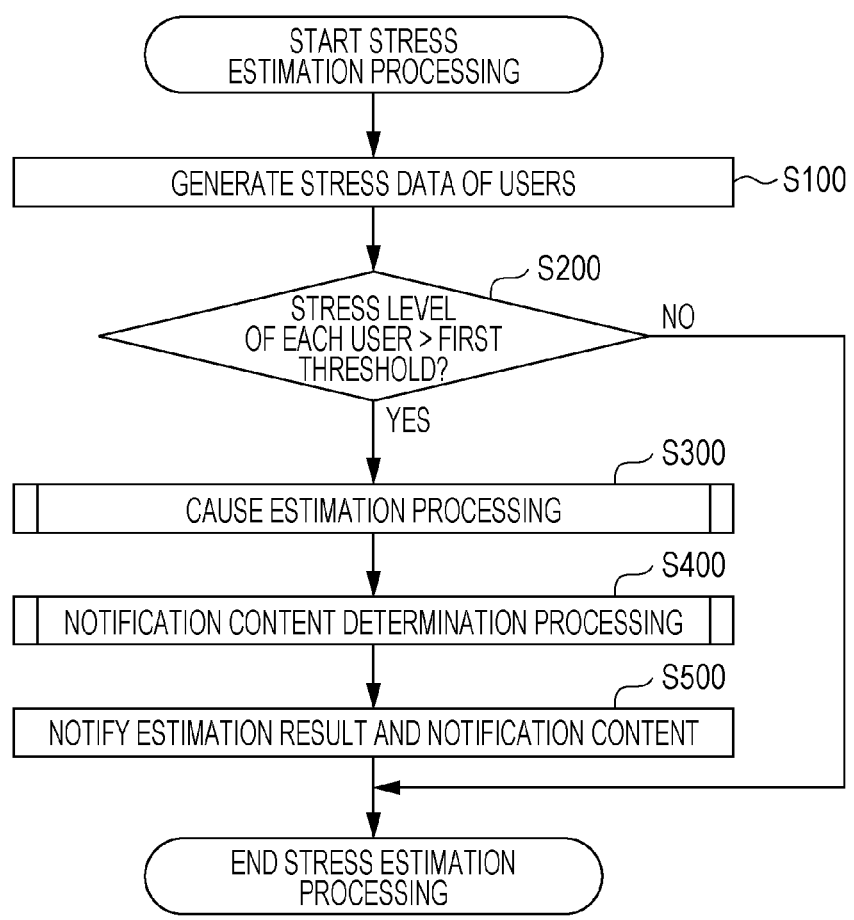
FIG. 7 is a flowchart for explaining the operation of stress estimation processing.

In the server 1, at predetermined timing such as predetermined time at night (e.g., 0 o'clock AM) or a periodical time interval (e.g., every two hours), stress estimation processing is performed by the controller 10. The stress estimation processing includes processing for, when determining using biological data that the user has stress, estimating a type and the like of the stress using life log data and notifying the user of a result of the estimation. Further, the stress estimation processing also includes processing for notifying notification content determined using the result of the estimation to a notification target person having a contact relation with the user determined using the result of the estimation. The operation of the stress estimation processing is explained below. FIG. 7 is a flowchart for explaining the operation of the stress estimation processing.

As illustrated in FIG. 7, when the stress estimation processing is started, the generator 11 generates, using the biological data of the users stored in the biological data storage 151, stress data indicating time series variations of stress levels of the users (S100).

S100 is explained in detail below. For example, it is assumed that the data illustrated in FIG. 4 is stored in the biological data storage 151. In this case, in S100, the generator 11 acquires one user ID "A" stored in the biological data storage 151.

Subsequently, the generator 11 refers to one or more biological data "a heart rate Ba11, a body temperature Ba12, a blood pressure Ba13, and perspiration Ba14" and "a heart rate Ba31, a body temperature Ba32, a blood pressure Ba33, and perspiration Ba34" associated with the one user ID "A" acquired from the biological data storage 151. As the order of the reference, the generator 11 refers to the biological data in order from the biological data having the earliest detection time point of the biological data indicated by dates and times associated with the respective biological data. The generator 11 refers to the biological data in the order of "Aug. 2, 2016 10:30" and "Aug. 2, 2016 11:30".

The generator 11 calculates a stress level at the detection time point "Aug. 2, 2016 10:30" of the one biological data "the heart rate Ba11, . . . " using the heart rate Ba11, the body temperature Ba12, the blood pressure Ba13, and the perspiration Ba14 included in the one biological data "the heart rate Ba11, . . . " referred to.

Specifically, the generator 11 calculates a product of the heart rate Ba11 and a predetermined first coefficient, a product of the body temperature Ba12 and a predetermined second coefficient, a product of the blood pressure Ba13 and a predetermined third coefficient, and a product of the perspiration Ba14 and a predetermined fourth coefficient and calculates a sum of the four products as a stress level. Note that, a method of calculating a stress level using biological data by the generator 11 is not limited to this and may be changed as appropriate according to items detected as biological data by the biological data detector 4.

Similarly, the generator 11 calculates, using the other biological data "the heart rate Ba31, . . . " of the acquired biological data, a stress level at a detection time point "Aug. 2, 2016 11:30" of the other biological data "the heart rate Ba11, . . . ".

The generator 11 generates data in which the calculated stress levels are arranged in the calculation order as stress data indicating a time series variation of a stress level of the user identified by the one user ID "A". Similarly, the generator 11 acquires another user ID stored in the biological data storage 151 and generates stress data indicating a time series variation of a stress level of a user identified by the acquired other user ID.

Referring back to FIG. 7, subsequently, the estimator 12 determines whether the stress levels included in the stress data of the users calculated in S100 exceed a predetermined first threshold (S200). When determining that a stress level of certain one user exceeds the first threshold (YES in S200), the estimator 12 determines that the one user has stress, sets the one user as a target user, and executes cause estimation processing for estimating a cause of the stress (S300).

Specifically, in the cause estimation processing in S300, the estimator 12 estimates a type of the stress of the target user using life log data corresponding to a detection time point of biological data that affects an increase in the stress level of the target user. When estimating that the stress of the target user is an interpersonal stress caused by contact with others, the estimator 12 further estimates an assailant, who is a cause of the interpersonal stress, using the life log data used for the estimation. Details of the cause estimation processing in S300 are explained below.

After S300, the notifier 13 executes notification content determination processing (S400). In the notification content determination processing in S400, the notifier 13 determines a notification target person out of people having a contact relation with the user using a result of the estimation in S300. The notifier 13 determines notification content notified to the notification target person using the result of the estimation. Details of the notification content determination processing in S400 are explained below.

After S400, the notifier 13 executes notification processing (S500). In the notification processing in S500, the notifier 13 notifies the target user of the result of the estimation in S300 and notifies the notification target person determined in S400 of the notification content determined in S400 (S500). After users determined as having stress levels exceeding the first threshold in S200 are set as target users and S300, S400, and S500 are respectively performed, the stress estimation processing ends. Consequently, it is possible to make the users and notification target persons having a contact relation with the users aware that the users have interpersonal stress to a degree at which the stress levels exceed the first threshold.

(Cause Estimation Processing)

Figure 8:
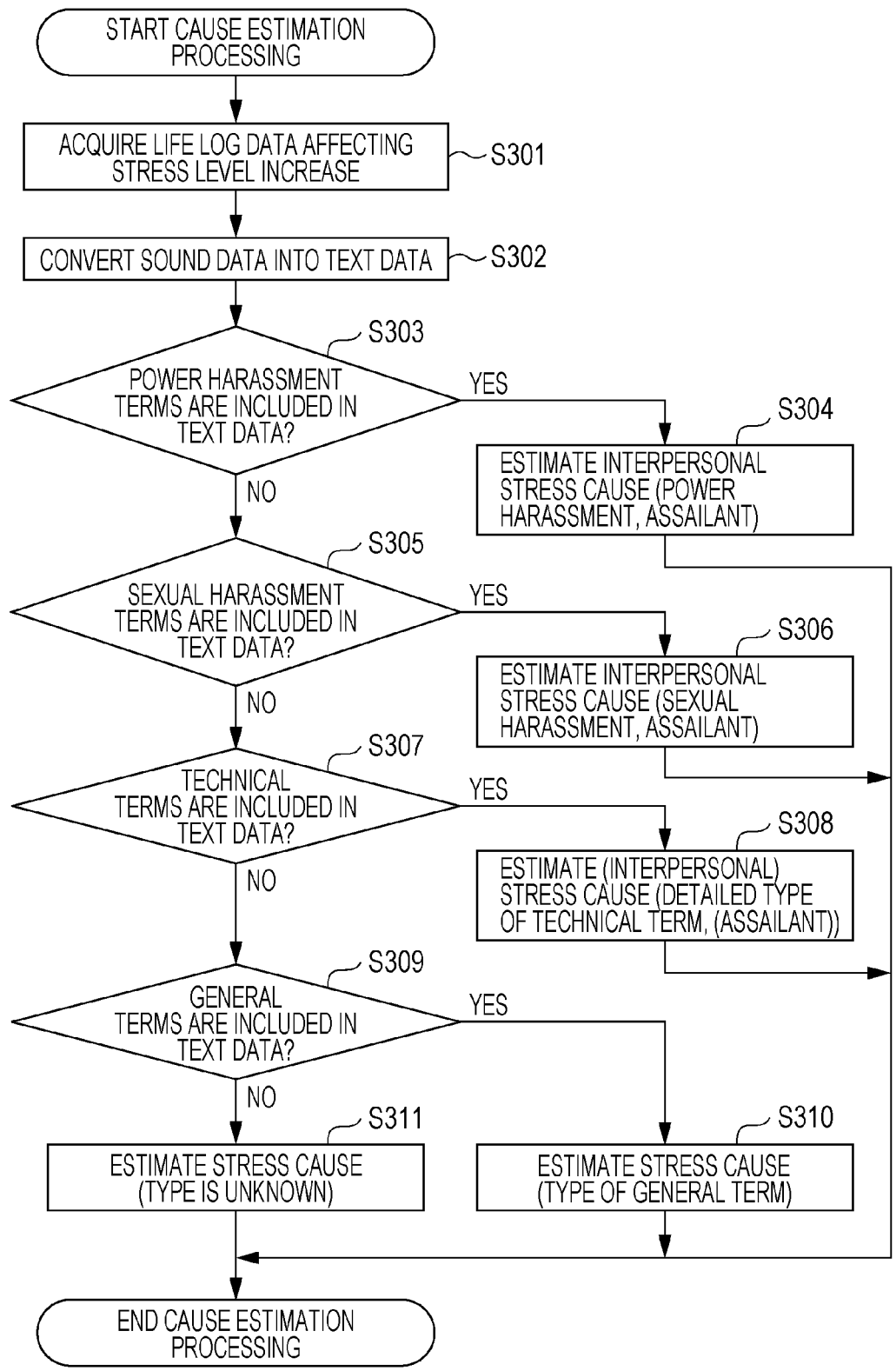
FIG. 8 is a flowchart for explaining the operation of cause estimation processing.

The cause estimation processing in S300 (FIG. 7) is explained in detail below. FIG. 8 is a flowchart for explaining the operation of the cause estimation processing. As illustrated in FIG. 8, when starting the cause estimation processing, the estimator 12 acquires life log data corresponding to a detection time point of biological data that affects an increase in a stress level (S301).

Specifically, in S301, the estimator 12 acquires, from the data (FIG. 4) stored in the biological data storage 151, a date (e.g., "Aug. 2, 2016) and time (e.g., "10:30") associated with the biological data (e.g., "the heart rate Ba11, . . . ") use for the calculation of the stress level determined as exceeding the first threshold in S200. Consequently, the estimator 12 grasps a time point (e.g., "Aug. 2, 2016 10:30") indicated by the acquired date and time as the detection time point of the biological data that affects the increase in the stress level.

The estimator 12 acquires life log data (e.g., "sound data A1") associated with a date and a time period (e.g., "Aug. 2, 2016" and "10:00 to 12:00") including the grasped detection time point (e.g., "Aug. 2, 2016 10:30") in the life log data (e.g., "sound data A1" and "sound data A3") associated with a user ID (e.g., "A") of the target user in the data (FIG. 6) stored in the life log storage 152. Consequently, the estimator 12 acquires life log data corresponding to the detection time point of the biological data that affects the increase in the stress level.

Subsequently, the estimator 12 converts sound data (e.g., "sound data A1") included in the life log data into text data indicating content of conversation at the time when the target user is acting (S302). Specifically, in S302, the estimator 12 executes publicly-known sound recognition processing to thereby recognize voice of conversation of people included in voice represented by the sound data included in the life log data acquired in S301 and generates text data indicating the content of the conversation.

Subsequently, the estimator 12 determines whether terms related to power harassment are included in the text data converted in S302 (S303). When determining that terms related to power harassment are not included in the text data converted in S302 (NO in S303), the estimator 12 determines whether terms related to sexual harassment are included in the text data (S305).

S303 and S305 are explained in detail below. FIG. 9 is a diagram illustrating an example of an interpersonal stress term table. For example, as illustrated in FIG. 9, an interpersonal stress term table in which types of interpersonal stress and terms related to the types of the interpersonal stress are associated is stored in the storage 15 in advance.

That is, in S303, the estimator 12 determines whether terms (e.g., "incompetent", "goldbricker", . . . ) associated with a type "power harassment" of the interpersonal stress in the interpersonal stress term table (FIG. 9) are included in the text data converted in S302. Similarly, in S305, the estimator 12 determines whether terms (e.g., "shall we go to meal?", "shall we go out for play?", . . . ) associated with a type "sexual harassment" of the interpersonal stress in the interpersonal stress term table (FIG. 9) are included in the text data converted in S302.

When determining in S303 that terms related to power harassment are included in the text data converted in S302 (YES in S303), the estimator 12 estimates that the target user has the interpersonal stress. Further, the estimator 12 estimates that a type of the interpersonal stress is "power harassment". Further, the estimator 12 estimates an assailant, who is a cause of the interpersonal stress, using the sound data before the conversion into the text data in S302 (hereinafter referred to as pre-conversion sound data) and the text data (S304). The estimator 12 ends the cause estimation processing.

When determining in S305 that terms related to sexual harassment are included in the text data converted in S302 (YES in S305), the estimator 12 estimates that the target user has the interpersonal stress. Further, the estimator 12 estimates that a type of the interpersonal stress is "sexual harassment". Further, the estimator 12 estimates an assailant, who is a cause of the interpersonal stress, using the pre-conversion sound data and the text data (S306). The estimator 12 ends the cause estimation processing.

A method of estimating an assailant, who is a cause of the interpersonal stress, in S304 and S306 is explained in detail below. In the storage 15, user IDs of the users and sound data indicating voices of the users (hereinafter referred to as user sound data) are stored in advance in association with each other.

When determining in S303 that terms related to power harassment are included in the text data converted in S302, in S304, the estimator 12 extracts sound data corresponding to the terms related to power harassment from the pre-conversion sound data. Similarly, when determining in S305 that terms related to sexual harassment are included in the text data converted in S302, in S304, the estimator 12 extracts sound data corresponding to the terms related to sexual harassment from the pre-conversion sound data.

In S304 and S306, the estimator 12 executes publicly-known voice print recognition processing to thereby specify, out of the user sound data stored in the storage 15, user sound data of a voice print matching a voice print of the extracted sound data. The estimator 12 acquires, from the storage 15, a user ID associated with the specified user sound data. The estimator 12 estimates a user identified by the acquired user ID as an assailant, who is a cause of the interpersonal stress.

On the other hand, when determining that terms related to sexual harassment are not included in the text data converted in S302 (NO in S305), the estimator 12 determines whether technical terms are included in the text data converted in S302 (S307).

S307 is explained in detail below. FIG. 10 is a diagram illustrating an example of data stored in the schedule storage 155. FIG. 11 is a diagram illustrating an example of a specialty type determination table. FIG. 12 is a diagram illustrating an example of a technical term table.

As illustrated in FIG. 10, in the schedule storage 155 illustrated in FIG. 2, a user ID (e.g., "A") of a user and schedule data indicating an action schedule of the user are stored in association with each other via the network 9 by an application in the smartphone 22 carried by the user, a personal computer not illustrated in the figure used by the user, or the like. The schedule data includes a date ("e.g., "Aug. 2, 2016") and a time period (e.g., "10:00 to 12:00") when the user is scheduled to act and content of a scheduled action (hereinafter referred to as action content) (e.g., "business trip").

As illustrated in FIG. 11, in the storage 15, a specialty type determination table in which a type (e.g., "task") of a technical term and terms (e.g., "business trip", "meeting", "paper work", . . . ) used as the action content included in the schedule data are associated with each other is stored in advance.

As illustrated in FIG. 12, in the storage 15, a technical term table in which a type (e.g., "task") of a technical term, a detail of the type of the technical term (hereinafter referred to as detailed type of the technical term) (e.g., "negotiation"), and technical terms (e.g., "transaction", "breakdown", . . . ) are associated with one another is stored in advance.

In S307, first, the estimator 12 refers to the data (FIG. 10) stored in the schedule storage 155 and acquires, among schedule data associated with the user ID (e.g., "A") of the target user, schedule data including the date (e.g., "Aug. 2, 2016") of the detection time point (e.g., "Aug. 2, 2016 10:30") of the biological data grasped in S301 and the time period (e.g., "10:00 to 12:00") including the time (e.g., "10:30") of the detection time point. Consequently, the estimator 12 acquires schedule data corresponding to the detection time of biological data that affects the increase in the stress level grasped in S301.

The estimator 12 refers to the specialty type determination table (FIG. 11) and acquires a type (e.g., "task") of a technical term associated with action content (e.g., "business trip") included in the acquired schedule data. Consequently, the estimator 12 grasps the acquired type of the technical term as a type of a technical term likely to be included in conversation during an action performed at the detection time point of the biological data.

The estimator 12 refers to technical terms "e.g., "transaction, "breakdown, . . . , "compliance", . . . , "progress", "minutes", "agenda", . . . ) associated with the acquired type (e.g., "task") of the technical term in the technical term table (FIG. 12) and determines whether the associated technical terms are included in the text data converted in S302.

When determining in S307 that a technical term (e.g., "breakdown") is included in the text data converted in S302 (YES in S307), the estimator 12 refers to the technical term table (FIG. 12) and estimates a detailed type (e.g., "negotiation") of a technical term associated with the technical term (e.g., "breakdown") as a type of the stress of the target user. Further, the estimator 12 estimates presence or absence of an assailant, who is a cause of the stress, using the pre-conversion sound data and the text data (S308). The estimator 12 ends the cause estimation processing.

Specifically, in S308, as in S304 and S306, the estimator 12 extracts, from the pre-conversion sound data, sound data corresponding to the technical term determined as being included in the text data in S307. The estimator 12 executes publicly-known voice print recognition processing to thereby determine whether user sound data of a voice print matching a voice print of the extracted sound data is present in the storage 15. When determining that user sound data of a voice print matching the voice print of the extracted sound data is present, the estimator 12 acquires a user ID associated with the user sound data from the storage 15. The estimator 12 estimates that a user identified by the acquired user ID is an assailant, who is a cause of the stress.

When estimating the assailant, who is the cause of the stress, in S308, the estimator 12 estimates that the user has interpersonal stress. In this case, the estimator 12 estimates, as a type of the interpersonal stress, a detailed type (e.g., "negotiation") of a technical term associated with the technical term in the technical term table (FIG. 12).

Note that, in S304, S306, and S308, the estimator 12 may refer to the data (FIG. 6) stored in the life log storage 152 and, when a plurality of user IDs (e.g., "A and B") associated with the life log data (e.g., "sound data A3") acquired in S301 are present, acquire a user ID (e.g., "B") different from the user ID (e.g., "A") of the target user among the plurality of user IDs. The estimator 12 may estimate that a user identified by the acquired user ID (e.g., "B") is an assailant, who is a cause of the interpersonal stress.

On the other hand, when determining in S302 that technical terms are not included in the text data converted in S302 (NO in S308), the estimator 12 determines whether general terms are included in the text data converted in S302 (S309).

S309 is explained in detail below. FIG. 13 is a diagram illustrating an example of a general term table. As illustrated in FIG. 13, a general term table in which a type (e.g., "golf") of a general term and general terms (e.g., "double bogie", . . . ) of the type are associated with each other is stored the storage 15 in advance. In S309, the estimator 12 determines whether general terms (e.g., "double bogie", . . . , "Hanshin", "Gamba", . . . ) stored in the general term table (FIG. 13) are included in the text data converted in S302.

When determining in S309 that a general term (e.g., "double bogie") is included in the text data converted in S302 (YES in S309), the estimator 12 estimates that the target user has stress caused by an emotion of the target user rather than the interpersonal stress. The estimator 12 estimates, as a type of the stress of the user, a type (e.g., "golf") of a general term associated with the general term in the general term table (FIG. 13) (S310). The estimator 12 ends the cause estimation processing.

On the other hand, when determining that a general term is not included in the text data converted in S302 (NO in S309), the estimator 12 estimates that the target user has stress of an unknown type (S311). The estimator 12 ends the cause estimation processing.

In this way, when estimating that the target user has the interpersonal stress in the cause estimation processing, the estimator 12 estimates a type of the interpersonal stress and an assailant, who is a cause of the interpersonal stress, using the life log data used for the estimation. Consequently, the type of the interpersonal stress of the target user and the assailant, who is the cause of the interpersonal stress, estimated in S500 (FIG. 7) are notified to the target user. Consequently, it is possible to make the target user aware contact with which person causes the interpersonal stress of the target user and what type of interpersonal stress the interpersonal stress is. As a result, the target user can easily take appropriate measures for reducing the interpersonal stress of the user.

(Notification Content Determination Processing)

Figure 14:
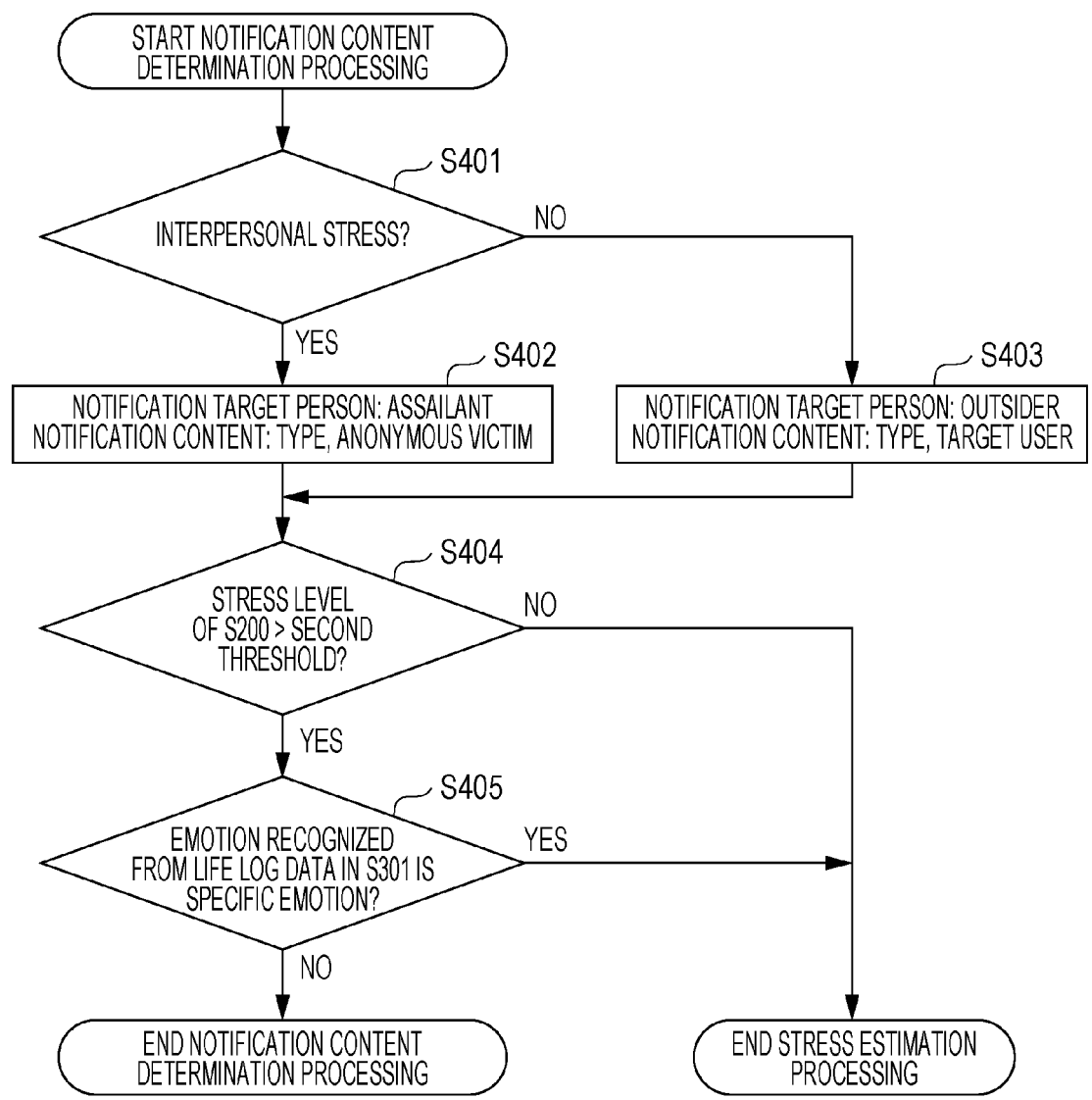
FIG. 14 is a flowchart for explaining the operation of notification-content determination processing.

Notification content determination processing in S400 (FIG. 7) is explained in detail below. FIG. 14 is a flowchart for explaining the operation of the notification content determination processing. As illustrated in FIG. 14, when starting the notification content determination processing, first, the notifier 13 determines whether it is determined in the cause estimation processing in S300 (FIG. 7) that the stress of the target user is estimated as the interpersonal stress (S401).

It is assumed that the notifier 13 determines that, in the cause estimation processing in S300, S304, S306, or S308 (FIG. 8) is performed and it is estimated that the stress of the target user is the interpersonal stress (YES in S401). In this case, the notifier 13 determines the assailant estimated in S300 as a notification target person. The notifier 13 determines to set, as notification content, the type of the interpersonal stress estimated in S300 and presence of an anonymous victim having the stress and generates a message indicating the notification content (e.g., "a user having stress because of your power harassment is present") (S402).

On the other hand, it is assumed that the notifier 13 determines that, in the cause estimation processing in S300, S310, or S311 (FIG. 8) is performed and it is estimated that the stress of the target user is not the interpersonal stress (NO in S401). In this case, the notifier 13 determines an outsider associated with the target user in advance as a notification target person. The notifier 13 determines to set, as notification content, the type of the stress estimated in S300 and the fact that the target user has the stress and generates a message indicating the notification content (S403).

S403 is explained in detail below. In the storage 15, profile data indicating user IDs and profiles and user IDs of one or more other users (outsiders) having a contact relation are stored in association with each other with respect to the users. These kinds of information are acquired from the smartphone 22 carried by the user or a personal computer or the like not illustrated in the figure used by the user via the network 9 and recorded in the storage 15.

In a profile of a user, a name (e.g., "Mr. A"), an age (e.g., "45"), sex (e.g., "male"), a type of industry 1 (e.g., "manufacturing") a type of industry 2 (e.g., "electrical machinery"), a type of task (e.g. "technical"), a title (e.g., "manager"), and hobbies (e.g., "golf, baseball, and drinking), which are characteristics of the user, are included. Note that the profile of the user is not limited to the above and may include, for example, an educational background and a birthplace.

In S403, the notifier 13 acquires contact user IDs associated with the user ID of the target user from the storage 15 and determines, as a notification target person, a user identified by a contact user ID different from the user ID of the assailant among the acquired contact user IDs. The notifier 13 determines to set, as notification content, the stress type estimated in S300 and the fact that the target user has the stress. The notifier 13 acquires a name of the target user from profile data associated with the user ID of the target user in the storage 15 and generates a message indicating the notification content (e.g., "Mr. A has stress of "negotiation").

After S402 and S403, the notifier 13 determines whether the stress level of the target user determined as exceeding the first threshold in S200 (FIG. 7) (hereinafter referred to as determined stress level) exceeds a second threshold associated in advance with the type of the stress included in the result of the estimation (S404).

The second threshold is a stress level serving as a determination standard for determining whether it is necessary to notify a user that the user has stress of a type. In the storage 15, second thresholds are stored in advance to correspond to respective types of stress that can be estimated in S300.

The types of stress that can be estimated in S300 include the types (e.g., "power harassment and "sexual harassment") of the respective kinds of interpersonal stress stored in the interpersonal stress term table (FIG. 9), the detailed types (e.g., "negotiation", "contract", . . . ) of the technical terms stored in the technical term table (FIG. 12), and the types (e.g., "golf" and "baseball") of the general terms stored in the general term table (FIG. 13). In the storage 15, the second threshold is stored in advance to correspond to stress of an unknown type that can be estimated in S311 (FIG. 8).

That is, in S404, the notifier 13 acquires, from the storage 15, the second threshold associated in advance with the type of the stress estimated in S300 and determines whether the determined stress level exceeds the acquired second threshold. Note that it is assumed that S311 (FIG. 8) is performed and a type of stress included in the result of the estimation is unknown. In this case, in S404, the notifier 13 acquires, form the storage 15, a second threshold, which is a stress level serving as a determination standard for determining whether it is necessary to notify the user that the user has stress of an unknown type.

When determining in S404 that the determined stress level does not exceed the second threshold (NO in S404), the notifier 13 does not perform the notification processing in S500 (FIG. 7).

Depending on a type of the stress of the target user, it is considered likely that the stress level of the target user is increased to the contrary by making the target user aware that the target user has the stress of the type. However, according to this aspect, even when the stress level of the target user exceeds the first threshold, when the stress level of the target user does not exceed the second threshold associated with the type of the stress in advance, the notifier 13 does not perform the notification processing in S500 (FIG. 7).

That is, according to this aspect, by deciding the second threshold as appropriate according to the type of the stress, it is possible to flexibly change determination on whether to notify the target user and the notification target person that the target user has the stress of the type corresponding to the second threshold. Consequently, it is possible to reduce the likelihood that the stress level of the target user is increased as explained above.

On the other hand, when determining in S404 that the determined stress level exceeds the second threshold (YES in S404), the notifier 13 determines whether an emotion of the target user recognized from the sound data included in the life log data acquired in S301 (FIG. 8) indicates a specific emotion indicating that the user has no stress (S405).

For example, in S405, the notifier 13 executes emotion estimation processing by publicly-known sound recognition to thereby respectively recognize degrees of emotions of joy, anger, grief, and pleasure of the target user from the sound data included in the life log data acquired in S301. If the recognized degree of joy and pleasure is larger than the recognized degree of anger and grief, the notifier 13 determines that the emotion of the target user is an emotion indicating that the target user has no stress. Note that a realization method of S405 is not limited to this. S405 may be realized by another method.

When determining in S405 that the emotion of the target user is the emotion indicating that the target user has no stress (YES in S405), the notifier 13 does not perform the notification processing in S500 (FIG. 7).

When the emotion of the target user recognized from the sound data included in the life log data acquired in S301 is the specific emotion indicating that the target user has no stress, the target user is considered to have no stress. Therefore, it is considered unnecessary to perform the notification processing in S500 (FIG. 7). According to this aspect, it is possible to avoid unnecessarily performing the notification processing in S500.

On the other hand, when determining in S405 that the emotion of the target user is not the emotion indicating that the target user has no stress (NO in S405), the notifier 13 ends the notification content determination processing.

(Notification Processing)

Figure 15:
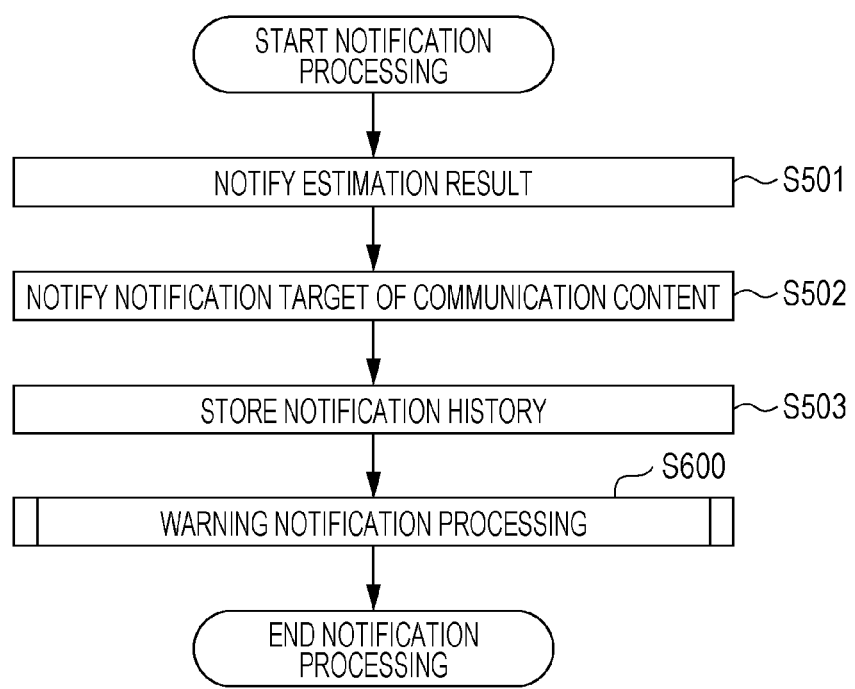
FIG. 15 is a flowchart for explaining the operation of notification processing.

The notification processing in S500 (FIG. 7) is explained in detail below. FIG. 15 is a flowchart for explaining the operation of the notification processing. As illustrated in FIG. 15, when starting the notification processing, first, the notifier 13 notifies the target user of the result of the estimation in S300 (FIG. 7) (S501).

S501 is explained in detail below. In the storage 15, a destination for making contact with the user of the stress management system 100 is stored in advance in association with a user ID of the user. The destination includes a mail address and an IP address of a personal computer used by the user.

In S501, the notifier 13 acquires, from the storage 15, a destination associated with the user ID of the target user. The notifier 13 causes the communicator 18 to transmit the result of the estimation in S300 to the acquired destination.

Consequently, when it is estimated that the stress of the target user is an interpersonal stress, a type of the interpersonal stress estimated as the stress of the target user and an assailant estimated as a cause of the interpersonal stress are notified to the target user. As a result, it is possible to make the target user aware contact with which person causes the interpersonal stress of the target user and what type of interpersonal stress the interpersonal stress is. Consequently, the target user can easily take appropriate measures for reducing the interpersonal stress of the target user.

When it is not estimated that the stress of the target user is an interpersonal stress, a type of stress estimated as the stress of the target user is notified to the target user. Consequently, it is possible to make the target user aware what type of stress the stress of the target user is. As a result, the target user can easily take appropriate measures for reducing the stress of the target user.

Subsequently, the notifier 13 notifies the notification content determined in S400 (FIG. 7) to the notification target person determined in S400 (S502). Specifically, in S502, the notifier 13 acquires, from the storage 15, a destination associated with a user ID of the notification target person. The notifier 13 causes the communicator 18 to transmit a message indicating the notification content generated in S402 or S403 to the acquired destination (FIG. 14).

Consequently, the message generated in S402 is notified to the assailant determined as the notification target person in S402. That is, the estimated type of the interpersonal stress and presence of a victim having stress because of the assailant are notified to the assailant estimated as a cause of the interpersonal stress of the target user. Consequently, it is possible to make the assailant aware that the assailant needs to refrain from an action that gives the interpersonal stress of the type to others.

The message generated in S403 is notified to the user identified by the contact user ID determined as the notification target person in S403. That is, the type of the stress estimated in S300 and the fact that the target user has the stress are notified to the user identified by the contact user ID. Consequently, it is possible to make the user identified by the contact user ID aware that the user needs to advise the target user that the target user refrain from an action that causes the stress of the type.

Subsequently, the notifier 13 stores, in the notification history storage 153, data indicating a history of notification to the target user and the notification target person (S503).

S503 is explained in detail below. FIG. 16 is diagram illustrating an example of data stored in the notification history storage 153 (FIG. 2). In S503, the notifier 13 stores the data illustrated in FIG. 16 in the notification history storage 153. Specifically, the notifier 13 stores a date when the estimation result is notified to the target user in S501 (hereinafter referred to as notification date; e.g., "Jul. 30, 2016") and time of the notification (hereinafter referred to as notification time; e.g., "0:00"), notification history data indicating content of the notification performed in S501 and S502, relaxation information, and human relation information in the notification history storage 153 in association with one another.

The notification history data includes a user ID of the target user (hereinafter referred to as target user ID; e.g., "C"), a date indicating the detection time point of the biological data affecting the increase in the stress level of the target user grasped in S301 (FIG. 8) (hereinafter referred to as detection date; e.g., "Jul. 29, 2016") and time indicating the detection time point (hereinafter referred to as detection time; e.g., "11:00"), and a type (e.g., "power harassment") of the stress estimated in S300 and a user ID of the assailant (hereinafter referred to as assailant ID; e.g., "A").

The notification history data includes a user ID of the notification target person determined in S400 (FIG. 7) (hereinafter referred to as notification target person ID) and a type of the notification in S502 (hereinafter referred to as notification type; e.g., "anonymous notification").

For example, it is assumed that, in S502, the notifier 13 notifies the message indicating that presence of the anonymous victim generated in S402 (FIG. 14) to the assailant determined as the notification target person in S402. In this case, in S503, the notifier 13 stores "anonymous notification", which is a notification type indicating that the presence of the anonymous victim is notified to the assailant.

On the other hand, it is assumed that, in S502, the notifier 13 notifies the message generated in S403 (FIG. 14) to an outsider associated with the target user in advance determined as the notification target person in S403. In this case, in S503, the notifier 13 stores "outsider notification", which is a notification type indicating that the message is notified to the outsider.

The relaxation information is information indicating whether the target user has relaxed the stress according to the notification. The relaxation information is used in stage notification processing explained below.

Specifically, in S503, the notifier 13 stores, as an initial value of the relaxation information, in the data (FIG. 16) stored in the notification history storage 153, relaxation information "un-relaxed" indicating that the stress of the target user is not relaxed (e.g., data in a second row to a fifth row in FIG. 16).

The human relation information is information indicating whether a human relation between the target user and the assailant is determined. The human relation information is used in relation determination processing explained below.

Specifically, in S503, the notifier 13 stores, as an initial value of the human relation information, in the notification history storage 153, human relation information "undetermined" indicating that the human relation between the target user and the assailant is not determined (e.g., the data in the second row to the fifth row in FIG. 16).

After S503, the notifier 13 performs warning notification processing (S600). The warning notification processing is notification for notifying the assailant of a warning indicating that at least a part of participants who participate in the action of the target user represented by the life log data used in the estimation in S300 and are different from the assailant estimated in S300 is likely to have the stress of the type estimated in S300.

(Warning Notification Processing)

Figure 17:
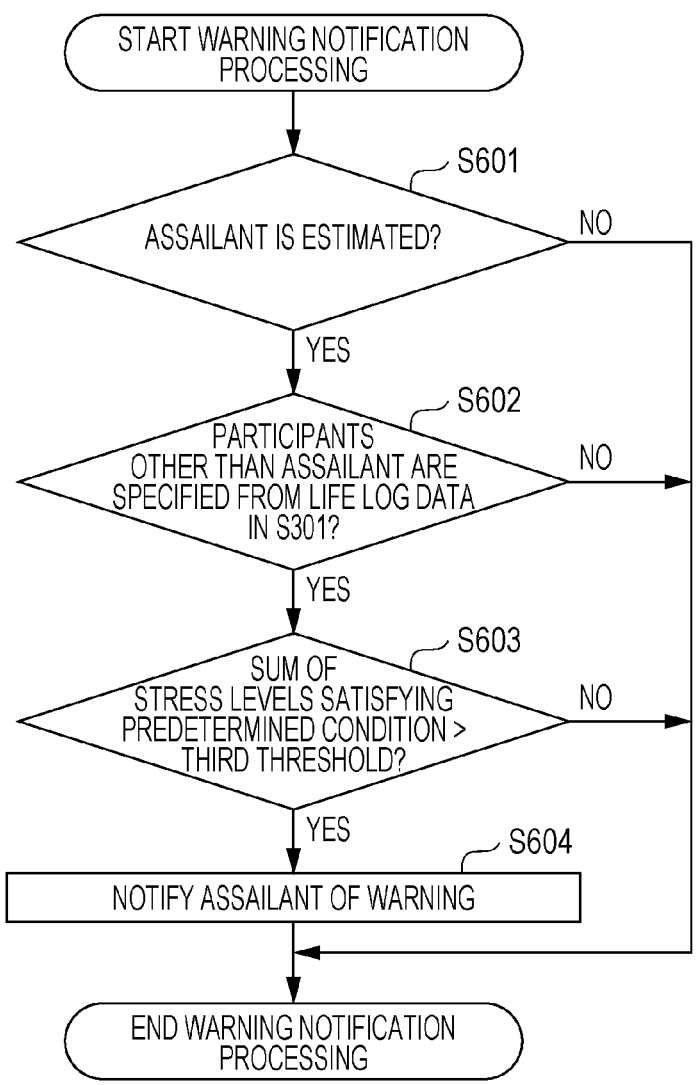
FIG. 17 is a flowchart for explaining the operation of warning notification processing.

The warning notification processing in S600 is explained in detail below. FIG. 17 is a flowchart for explaining the operation of the warning notification processing. As illustrated in FIG. 17, when starting the warning notification processing, first, the notifier 13 determines whether an assailant is estimated in S300 (S601).

When determining in S601 that an assailant is not estimated (NO in S601), an assailant to whom the warning is notified is absent and therefore the notifier 13 ends the warning notification processing.

On the other hand, when determining in S601 that an assailant is estimated (YES in S601), the notifier 13 specifies, using the life log data acquired in S301, participants who participate in an action (a first action) of the target user represented by the life log data and are different from the assailant (S602).

S602 is explained in detail below. In S602, by executing publicly-known voice print recognition processing, the notifier 13 determines whether sound data including a voice print matching the voice print of the user sound data stored in the storage 15 is present among the sound data included in the life log data acquired in S301.

When determining that sound data including the matching voice print is present, the notifier 13 acquires, from the storage 15, user IDs different from the user ID of the assailant among user IDs corresponding to the sound data. Consequently, the notifier 13 specifies users identified by the acquired user IDs as participants who participate in the action of the target user and are different from the assailant. On the other hand, when determining that sound data including the matching voice print is absent or when user IDs different from the user ID of the assailant cannot be acquired, the notifier 13 does not specify participants who participate in the action of the target user and are different from the assailant.

It is assumed that, in S602, the notifier 13 specifies participants who participate in the action of the target user and are different from the assailant (YES in S602). In this case, the notifier 13 determines whether a sum of stress levels satisfying a predetermined condition among stress levels corresponding to an action time of the specified participants exceeds a predetermined third threshold (S603).

S603 is explained in detail below. In S603, first, the notifier 13 refers to the data (FIG. 6) stored in the life log storage 152 and acquires a date (e.g., "Aug. 2, 2016") and a time period (e.g., "10:00 to 12:00") associated with the life log data (e.g., "sound data A1") acquired in S301. Consequently, the notifier 13 grasps a period (e.g., "Aug. 2, 2016 10:00 to 12:00") indicated by the acquired date and the acquired time period as a period in which the action of the target user represented by the life log data is performed (hereinafter referred to as action period).

The notifier 13 causes the generator 11 to generate, concerning the participants specified in S602, stress data indicating a time series variation of a stress level in the action period (hereinafter referred to as participant stress data). Specifically, as in S100 (FIG. 7), the notifier 13 refers to the data (FIG. 4) stored in the biological data storage 151, acquires biological data associated with the user IDs of the participants and the date and the time included in the action period, and causes the generator 11 to generate participant stress data of the participants.

Subsequently, the notifier 13 acquires a stress level satisfying a predetermined condition among stress levels included in the generated participant stress data of the participants. In this embodiment, it is assumed that the stress level satisfying the predetermined condition is a maximum stress level included in the participant stress data of the participants. That is, the notifier 13 acquires maximum values of stress levels respectively from the participant stress data of the participants. The notifier 13 determines whether a sum of the acquired maximum values of the stress levels exceeds the third threshold.

Note that the stress level satisfying the predetermined condition is not limited to this and may be, for example, a stress level generated using biological data at a time point closest to a time point when the stress level of the target user exceeds the first threshold, among the participant stress data of the participants. As the stress level satisfying the predetermined condition, a predetermined number of stress levels may be acquired in order from a largest stress level out of the stress levels included in the participant stress data of the participants.

It is assumed that, in S603, the notifier 13 determines that the sum of the acquired maximum values of the stress levels exceeds the third threshold (YES in S603). In this case, the notifier 13 notifies the assailant of a warning indicating that at least a part of the participants are likely to have the interpersonal stress of the type estimated in S300 because of the assailant estimated in S300 (S604).

For example, in S604, the notifier 13 generates a message (e.g., "at least a part of participants of an action in Aug. 2, 2016 10:00 to 12:00 are likely to have stress because of your power harassment") using the type of the interpersonal stress estimated in S300 and the action period (e.g., "Aug. 2, 2016 10:00 to 12:00") grasped in S603. As in S502 (FIG. 15), the notifier 13 notifies the assailant of the message.

As explained above, it is assumed that the sum of the stress levels satisfying the predetermined condition exceeds the third threshold. In this case, it is considered that participants acting together with the target user are also likely to have the same interpersonal stress as the interpersonal stress of the target user while repeating contact with the assailant.

However, according to this aspect, the assailant is notified that at least a part of the participants are likely to have the same interpersonal stress as the interpersonal stress of the target user because of the assailant. Consequently, it is possible to make the assailant aware in advance such that the participants do not have the same interpersonal stress as the interpersonal stress of the target user. That is, it is possible to make the assailant aware that the assailant needs to refrain from an action that the assailant performed on the target user.

Second Embodiment

Figure 18:
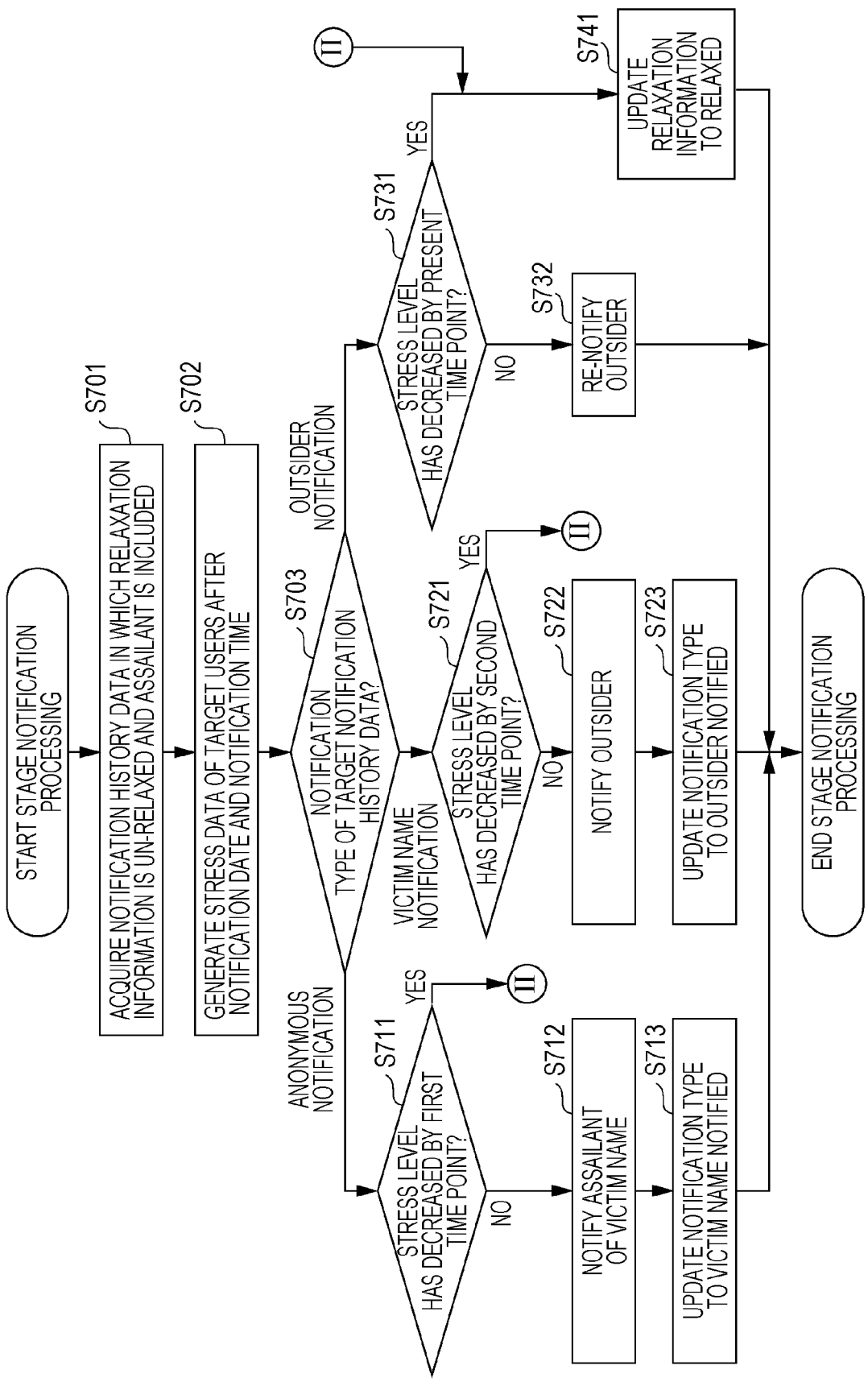
FIG. 18 is a flowchart for explaining the operation of stage notification processing.

In the first embodiment, when it is estimated that the stress of the target user is estimated as the interpersonal stress in the cause estimation processing in S300 (FIG. 7), in S502 (FIG. 15), the message generated in S402 (FIG. 14) is notified to the assailant determined as the notification target person in S402. However, the notifier 13 may execute stage notification processing illustrated in FIG. 18 to thereby change a notification method stepwise. FIG. 18 is a flowchart for explaining the operation of the stage notification processing.

Specifically, the notifier 13 starts the stage notification processing at predetermined timing such as predetermined time at night (e.g., 1 o'clock AM). As illustrated in FIG. 18, when starting the stage notification processing, first, the notifier 13 acquires, from the data (FIG. 16) stored in the notification history storage 153, notification history data in which relaxation information is "un-relaxed" and an assailant ID is included (e.g., notification history data in a third row to a fifth row in FIG. 16) (S701). Consequently, the notifier 13 acquires notification history data in which notification performed to that point does not contribute to relaxation of interpersonal stress of a target user.

The notifier 13 causes the generator 11 to generate, using the acquired notification history data, in the data (FIG. 16) stored in the notification history storage 153, stress data of a target user identified by a target user ID included in the notification history data after a time point indicated by a notification date and notification time (hereinafter referred to as notification time point) associated with the notification history data (hereinafter referred to as post-notification stress data) (S702).

Specifically, in S702, as in S100 (FIG. 7), the notifier 13 causes the generator 11 to generate post-notification stress data of the target user identified by the target user ID using the same user ID as the target user ID included in the notification history data and biological data associated with a date and time after the notification time point in the data (FIG. 4) stored in the biological data storage 151.

The notifier 13 performs processing in S703 and subsequent steps targeting the notification history data acquired in S701. In the following explanation, the notification history data set as the target of the processing in S703 and subsequent steps is referred to as target notification history data.

Specifically, if a notification type included in the target notification history data is "anonymous notification" ("anonymous notification" in S703), the notifier 13 determines whether there is a stress level decreased below the first threshold by a first time point when a first predetermined time elapses from the notification time point in the post-notification stress data generated in S702 (S711).

Consequently, the notifier 13 notifies, in S501 (FIG. 15), the target user of the result of the estimation in S300 and determines, in S502 (FIG. 15), whether a stress level of the target user has decreased below the first threshold by the first time point when the first predetermined time elapses from a time point when the notification content determine in S402 (FIG. 14) is notified to the assailant.

When determining in S711 that a stress level decreased below the first threshold is absent (NO in S711), the notifier 13 determines that the stress level of the target user has not decreased below the first threshold by the first time point. In this case, the notifier 13 further notifies the assailant that an anonymous victim notified last time is the target user (S712).

Specifically, in S712, the notifier 13 acquires a name and the like of the target user from profile data associated with the same user ID as a target user ID included in the target notification history data in the storage 15. The notifier 13 generates a message (e.g., "a victim notified last time is Mr. D") indicating that the anonymous victim notified last time is the target user represented by the acquired name and the like. As in S502 (FIG. 15), the notifier 13 notifies the generated message to an assailant identified by an assailant ID included in the target notification history data.

Consequently, it is possible to make the assailant aware that the assailant needs to refrain from an action that gives the interpersonal stress estimated in S300 to the target user.

The notifier 13 updates, in the data (FIG. 16) stored in the notification history storage 153, the notification type included in the target notification history data to "victim name notified" indicating that a victim name is notified (S713; e.g., data in a fourth row in FIG. 16). Consequently, the notifier 13 ends the processing in S703 and subsequent steps that targets the target notification history data.

On the other hand, if the notification type included in the target notification history data is "victim name notified" ("victim name notified" in S703), as in S711, the notifier 13 determines whether a stress level decreased below the first threshold by a second time point when a second predetermined time elapses from the first time point is present in the post-notification stress data generated in S702 (S721). Consequently, the notifier 13 determines whether the stress level of the target user (the first user) has decreased below the first threshold by the second time point.

When determining in S721 that a stress level decreased below the first threshold is absent (NO in S721), the notifier 13 determines that the stress level of the target user has not decreased below the first threshold by the second time point. In this case, the notifier 13 notifies an outsider associated with the assailant in advance that the target user has the interpersonal stress estimated in S300 because of the assailant (S722).

Specifically, in S722, the notifier 13 acquires the name and the like of the target user from the profile data associated with the same user ID as the target user ID included in the target notification history data in the storage 15. Similarly, the notifier 13 acquires a name and the like of the assailant from the profile data associated with the same user ID as an assailant user ID included in the target notification history data in the storage 15. The notifier 13 generates a message (e.g., "Mr. D has stress because of power harassment of Mr. A") indicating that the target user indicated by the acquired name and the like of the target user has the interpersonal stress estimated in S300 because of the assailant indicated by the acquired name and the like of the assailant.

As in S403 (FIG. 15), the notifier 13 acquires, from the storage 15, contact user IDs associated with the same user ID as the assailant user ID included in the target notification history data. The notifier 13 grasps, as an outsider associated with the assailant in advance, a user identified by a contact user ID different from the assailant user ID among the acquired contact user IDs. As in S502 (FIG. 15), the notifier 13 notifies the outsider of the generated message.

Consequently, it is possible to make the outsider associated with the assailant in advance aware that the outsider needs to advise the assailant that the assailant refrain from an action that gives the interpersonal stress estimated in S300 (FIG. 7) to the target user.

The notifier 13 updates, in the data (FIG. 16) stored in the notification history storage 153, the notification type included in the target notification history data to "outsider notified" indicating that notification to the outsider is performed (S723; e.g., data in a third row in FIG. 16). Consequently, the notifier 13 ends the processing in S703 and subsequent steps that targets the target notification history data.

When determining in S703 that the notification type included in the target notification history data is "outsider notified" ("outsider notified" in S703), as in S711 and S721, the notifier 13 determines whether a stress level decreased below the first threshold from the second time point to the present time point is present in the post-notification stress data generated using the target notification history data in S702 (S731). Consequently, the notifier 13 determines whether the stress level of the target user has decreased below the first threshold by the present time point.

When determining in S731 that a stress level decreased below the first threshold is absent (NO in S731), the notifier 13 determines that the stress level of the target user has not decreased below the first threshold by the present time point. In this case, as in S722, the notifier 13 notifies the outsider associated with the assailant in advance again that the target user has a stress of the type of the interpersonal stress included in the result of the estimation in S300 because of the assailant (S732). Consequently, the notifier 13 ends the processing in S703 and subsequent steps in which the target notification history data is used. In this case, it is possible to make the outsider associated with the assailant in advance again that the outsider needs to advise the assailant that the assailant refrain from an action that gives the interpersonal stress of the type included in the result of the estimation in S300 (FIG. 7) to the target user.

On the other hand, it is assumed that, in S711, S721, and S731, the notifier 13 determines that a stress level decreased below the first threshold is present (YES in S711, YES in S721, and YES in S731). In these cases, the notifier 13 determines that the stress level of the target user has already decreased below the first threshold and determines that the stress of the target user has already been relaxed. In these cases, the notifier 13 updates, in the data (FIG. 16) stored in the notification history storage 153, the relaxation information associated with the target notification history data to "relaxed" indicating that the stress of the target user has been relaxed (S741). Consequently, the notifier 13 ends the processing in S703 and subsequent steps that targets the target notification history data.

When ending the processing in S703 and subsequent steps that targets the notification history data acquired in S701, the notifier 13 ends the stage notification processing.

Third Embodiment

Figure 19:
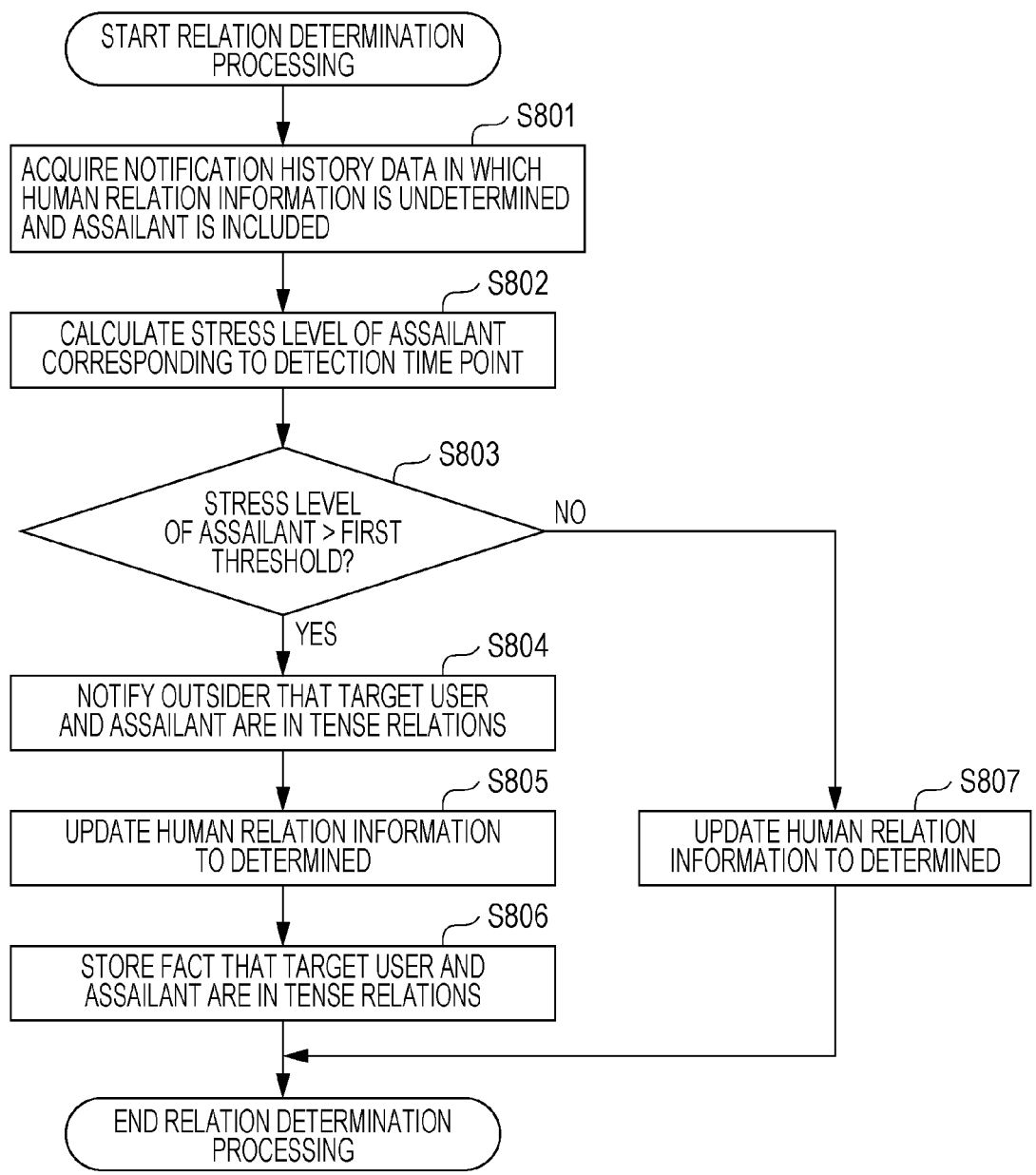
FIG. 19 is a flowchart for explaining the operation of relation determination processing.

In the configurations explained in the first and second embodiments, the notifier 13 may further execute relation determination processing illustrated in FIG. 19. That is, the notifier 13 may determine whether the target user estimated as having the interpersonal stress and the assailant estimated as being the cause of the interpersonal stress in the cause estimation processing in S300 (FIG. 7) are in tense relations. FIG. 19 is a flowchart for explaining the operation of the relation determination processing.

Specifically, the notifier 13 starts the relation determination processing at predetermined timing such as predetermined time at night (e.g., 2 o'clock AM). As illustrated in FIG. 19, when starting the relation determination processing, first, the notifier 13 acquires, from the data (FIG. 16) stored in the notification history storage 153, notification history data in which the human relation information is "undetermined" and the assailant ID is included (e.g., the notification history data in the third row to the fifth row in FIG. 16) (S801). Consequently, the notifier 13 acquires notification history data in which a human relation between the target user having the interpersonal stress and the assailant is not determined.

The notifier 13 performs processing in S802 and subsequent steps targeting the notification history data acquired in S801. In the following explanation, the notification history data set as the target of the processing in S802 and subsequent steps is referred to as target notification history data.

Specifically, first, the notifier 13 grasps, using the target notification history data, a detection time point of biological data of the target user corresponding to the stress level determined as exceeding the first threshold in S200 (FIG. 7). The notifier 13 causes the generator 11 to generate a stress level of the assailant at a time point corresponding to the grasped detection time point (S802). Consequently, the notifier 13 causes the generator 11 to generate a stress level of the assailant at a time point when the stress level of the target user increases.

S802 is explained in detail below. In S802, first, the notifier 13 acquires a target user ID, a detection date, detection time, and an assailant ID included in the target notification history data (FIG. 16). Consequently, the notifier 13 grasps a time point indicated by the detection date and the detection time as a detection time point of biological data corresponding to the stress level determined as exceeding the first threshold in S200 (FIG. 7).

The notifier 13 acquires, from the biological data storage 151 (FIG. 4), biological data at a time point closest to the grasped detection time point among biological data associated with the same user ID as the assailant ID. The notifier 13 causes the generator 11 to calculate a stress level of the assailant using the acquired biological data according to the same calculation method as in S100 (FIG. 7). Consequently, the notifier 13 causes the generator 11 to calculate a stress level of the assailant at a time point corresponding to the detection time point.

Note that a method of calculating a stress level of the assailant in S802 is not limited to this. For example, the notifier 13 may refer to the data (FIG. 6) stored in the life log storage 152 and grasp, as the time point corresponding to the detection time point, a date and a time period including the detection time point among dates and time periods associated with the same user ID as the target user ID. Accordingly, the notifier 13 may acquire, from the biological data storage 151 (FIG. 4), biological data associated with a date and time included in the acquired date and the acquired time period among the biological data associated with the same user ID as the assailant ID. The notifier 13 may cause the generator 11 to calculate a stress level of the assailant using the acquired biological data.

Subsequently, the notifier 13 determines whether the stress level of the assailant generated in S802 exceeds the first threshold (S803). Consequently, the notifier 13 determines whether the stress level of the assailant at the time point corresponding to the detection time point exceeds the first threshold.

It is assumed that, in S803, the notifier 13 determines that the stress level of the assailant calculated in S802 exceeds the first threshold (YES in S803). In this case, the notifier 13 determines that the assailant gives an interpersonal stress to the target user but the assailant also has stress. In this case, the notifier 13 determines that the target user and the assailant are in tense relations and notifies an outsider associated with each of the target user and the assailant in advance that the target user and the assailant are in the tense relations (S804).

Specifically, in S804, the notifier 13 acquires names of the target user and the assailant from profile data associated with the user IDs of the target user and the assailant in the storage 15 and generates a message (e.g., "Mr. D and Mr. A are in tense relations") indicating that the target user and the assailant are in the tense relations. As in S722 (FIG. 18), the notifier 13 grasps an outsider associated with each of the target user and the assailant in advance and notifies the grasped outsider of the message.

When the target user and the assailant are in the tense relations, if the target user and the assailant come into contact, the stress levels of the target user and the assailant are considered to increase. According to this aspect, when both of the stress levels of the target user and the assailant exceed the first threshold, it is determined that the target user and the assailant are in the tense relations and the outsider associated with each of the target user and the assailant in advance is notified that the user and the assailant are in the tense relations. Consequently, it is possible to appropriately determine that the target user and the assailant are in the tense relations and make the outsider aware of a result of the determination.

Subsequently, the notifier 13 updates, in the data (FIG. 16) stored in the notification history storage 153, the human relation information associated with the target notification history data to "determined" indicating that a human relation between the target user and the assailant is determined (S805).

Further, the notifier 13 stores a determination result in S804, that is, the fact that the target user and the assailant are in the tense relations in the human map storage 154 illustrated in FIG. 2 (S806). Consequently, the notifier 13 ends the processing in S802 and subsequent steps on the target notification history data.

S806 is explained in detail below. FIG. 20 is a diagram illustrating an example of data stored in the human map storage 154. Specifically, as illustrated in FIG. 20, a date when a human relation among a plurality of users identified by a plurality of user IDs is determined (hereinafter referred to as determination date), the plurality of user IDs, and relation information (e.g., "tense") indicating a human relation among the plurality of users are stored in association with one another in the human map storage 154.

Specifically, in S806, the notifier 13 sets the target user ID and the assailant ID included in the target notification history data as a plurality of user IDs (e.g., "D and A"). The notifier 13 stores a determination date (e.g., "Aug. 2, 2016") when it is determined that the target user and the assailant are in the tense relations, the plurality of user IDs (e.g., "D and A"), and "tense", which is the relation information indicating that the target user and the assailant are in the tense relation, in the human map storage 154 in association with one another.

According to this aspect, when both of the stress levels of the target user and the assailant exceed the first threshold, the fact that the target user and the assailant are in the tense relations is stored in the human map storage 154. Consequently, it is possible to make the user, who refers to the data stored in the human map storage 154, aware of this determination result.

On the other hand, it is assumed that, in S803, the notifier 13 determines that the stress level of the assailant generated in S802 does not exceed the first threshold (NO in S803). In this case, the notifier 13 determines that the assailant gives interpersonal stress to the target user in a state in which the assailant has no stress and determines that the target user and the assailant are not in the tense relations.

In this case, the notifier 13 updates, in the data (FIG. 16) stored in the notification history storage 153, the human relation information associated with the target notification history data to "determined" indicating that a human relation between the target user and the assailant is determined (S807). Consequently, the notifier 13 ends the processing in S802 and subsequent steps on the target notification history data.

When ending the processing in S802 and subsequent steps that targets the notification history data acquired in S801, the notifier 13 ends the relation determination processing.

Note that the first to third embodiments are only illustrations of the embodiments according to the present disclosure and are not meant to limit the embodiments to the first to third embodiments. For example, modified embodiments explained below may be adopted.

First Modified Embodiment

In the first to third embodiments, it is assumed that the sound data including the voice of the user is included in the life log data. However, the present disclosure is not limited to this. Image data including an image of the user may be included in the life log data.

In this case, the user IDs of the users and image data including face images of the users (hereinafter referred to as user image data) may be stored in the storage 15 in association with each other. In S304, S306, and S308 (FIG. 8), when the estimator 12 estimates an assailant, the estimator 12 may recognize a face image of a person from image data included in the life log data by performing publicly-known image recognition processing. The estimator 12 may acquire, from the storage 15, a user ID that is associated with a face image having a feature value approximately equal to a feature value of the recognize face image and is different from the user ID of the target user. The estimator 12 may estimate that a user identified by the acquired user ID is an assailant who causes stress.

In this case, in S405 (FIG. 14), the notifier 13 may determine whether an expression of the target user recognized from the image data included in the life log data indicates a predetermined expression indicating that the target user has no stress instead of determining whether emotion of the target user recognized from the sound data included in the life log data acquired in S301 indicates specific emotion indicating that the target user has no stress.

Specifically, in S405, by executing publicly-known image recognition processing, the notifier 13 may recognize a face image of the target user from the image data included in the life log data acquired in S301. By executing the publicly-known image recognition processing, when a feature value indicating an expression of the target user represented by the recognized face image is closer to a feature value indicating an expression of joy and pleasure than a feature value indicating an expression of anger and grief, the notifier 13 may determine that an expression of the target user is an expression indicating that the target user has no stress. Note that the realization method of S405 is not limited to this. S405 may be realized by another method.

In this case, when determining in S405 that the expression of the target user is the expression indicating that the target user has no stress (YES in S405), the notifier 13 does not perform the notification processing in S500 (FIG. 7). When it is determined in S405 that the expression of the target user is the expression indicating that the target user has no stress, the target user is considered to have no stress. Therefore, it is considered unnecessary to perform notification of the result of the estimation in S300 (FIG. 7) and the notification content determined in S402 or S403. According to this aspect, it is possible to avoid unnecessarily performing notification in such a case.

Second Modified Embodiment

The stress management system 100 does not have to include the monitoring device 3. In that case, for example, the smartphone 22 including the biometric sensor may include the life log detector 5 in addition to the biological data detector 4 illustrate in FIG. 2.

Third Modified Embodiment

The schedule storage 155 of the storage 15 illustrated in FIG. 2 and S307 and S308 illustrated in FIG. 8 may be omitted.

Fourth Modified Embodiment

In FIG. 1, instead of the card reader 33, a card reader having the same functions may be incorporated in the individual identification card 23. When another user having the individual identification card 23 approaches the user having the individual identification card 23, the card reader incorporated in the individual identification card 23 may acquire profile data stored in the memory chip in the individual identification card 23 of the other user. The card reader incorporated in the individual identification card 23 may transmit predetermined information (e.g., a user ID) included in the acquired profile data to the server 1.

For example, it is assumed that a user has interpersonal stress and an assailant, who is a cause of the interpersonal stress, approaches the user. At this point, even if the user is not aware of the approach of the assailant, the card reader incorporated in the individual identification card 23 of the user can acquire the profile data stored in the memory chip of the personal identification card 23 of the assailant and transmit a user ID of the assailant to the server 1 together with a user ID of the user. Consequently, the server 1 can grasp that the user and the assailant approach each other.

When estimating in S300 (FIG. 7) that the user is a user having interpersonal stress, as in S501, the server 1 may transmit, to the user, a message indicating that the assailant approaches (FIG. 7). In this way, the server 1 may make the user aware of the approach of the assailant.

Fifth Modified Embodiment

S405 (FIG. 14) may be omitted.

Sixth Modified Embodiment

S600 (FIG. 15) may be omitted.

Seventh Modified Embodiment

S404 (FIG. 14) may be omitted.

Eighth Modified Embodiment

In S402 (FIG. 14), when determining that it is estimated in the cause estimation processing in S300 that the stress of the target user is not interpersonal stress (NO in S401), the notifier 13 does not have to perform the processing in S403 and subsequent steps.

Ninth Modified Embodiment

In S304, S306, and S308 (FIG. 8), the estimator 12 does not have to estimate a type of the stress and an assailant, who is a cause of the stress. Accordingly, S402 may be omitted.

The technique of the present disclosure is useful in preventing members of an organization such as a company or a school from continuing to have interpersonal stress.

What is claimed is:

1. A stress management system, comprising:
   at least one biometric sensor that detects a heart rate, a body temperature, a blood pressure and perspiration of a user;
   a microphone that detects sound data, as life log data, from an environment around the user;
   a memory that stores instructions; and
   a processor, when executing the instructions stored in the memory, that performs operations including:
   generating stress data indicating a time series variation of a stress level of the user, the stress level being determined by summing a product of the heart rate and a first coefficient, a product of the body temperature and a second coefficient, a product of the blood pressure and a third coefficient, and a product of the perspiration and a fourth coefficient;
   detecting that the stress level of the user included in the stress data exceeds a first threshold, and a time at which the stress level exceeds the first threshold;
   in response to detecting that the stress level of the user included in the stress data exceeds the first threshold, determining whether or not stress of the user is interpersonal stress caused by contact with another person, using the sound data at the detected time;
   in response to determining that the stress of the user is interpersonal stress, determining an assailant, as a notification target person, who is a cause of the stress, by performing a voice print matching using the sound data at the detected time, and notifying, via a network, the user of a result of the determination, and notifying the assailant that an anonymous victim has the stress classified as interpersonal stress because of the assailant; and
   in response to determining that the stress of the user is not interpersonal stress, notifying, via the network, an outsider, as the notification target person, who is associated with the user, that the user has stress other than the interpersonal stress.

2. The stress management system according to claim 1, wherein
in response to determining that the stress of the user is interpersonal stress, a type of interpersonal stress is further determined, and
the processor further notifies the assailant of the determined type of interpersonal stress.

3. The stress management system according to claim 2, wherein, in response to determining that the stress level of the user does not fall below the first threshold by a first point in time when a first period elapses from the notification to the assailant, the processor further notifies the assailant that the anonymous victim is the user.

4. The stress management system according to claim 3, wherein, in response to determining that the stress level of the user does not fall below the first threshold by a second point in time when a second period elapses from the first point in time, the processor further notifies an outsider previously associated with the assailant that the user has the stress classified as the type of interpersonal stress because of the assailant.

5. The stress management system according to claim 2, wherein,
the processor further determines whether a stress level of the assailant exceeds the first threshold at a first point in time corresponding to a point in time when the stress level of the user exceeds the first threshold,
in response to determining that the stress level of the assailant exceeds the first threshold at the first point in time, the processor further notifies an outsider previously associated with each of the user and the assailant that the user and the assailant are in tense relations.

6. The stress management system according to claim 2, further comprising a human map storage, wherein
the processor further determines whether a stress level of the assailant exceeds the first threshold at a first point in time corresponding to a point in time when the stress level of the user exceeds the first threshold,
in response to determining that the stress level of the assailant exceeds the first threshold at the first point in time, the processor stores, in the human map storage, information indicating that the user and the assailant are in tense relations.

7. The stress management system according to claim 1, wherein
in response to determining that the stress of the user is not interpersonal stress, the processor further determines a type of the stress using the sound data, and
the processor notifies the outsider that the user has the stress classified as the determined type.

8. The stress management system according to claim 1, wherein
the processor further determines a type of the stress of the user using the sound data,
the processor determines whether or not the stress level of the user exceeds a second threshold previously associated with the type of the stress, and
in response to determining that the stress level of the user exceeds the first threshold, and does not exceed the second threshold, the processor does not notify the user of the result and does not notify the notification target person of a notification content.

9. The stress management system according to claim 2, wherein,
the processor further determines whether or not a sum of stress levels satisfying a predetermined condition among stress levels of participants exceeds a second threshold,
in response to determining that the sum of stress levels satisfying the predetermined condition exceeds the second threshold, the processor further notifies the assailant that the participants are likely to have stress classified as the type of interpersonal stress because of the assailant, action histories of the participants being included in the life log data at a point in time corresponding to a point in time when the stress level of the user exceeds the first threshold, the participants being different from the assailant.

10. The stress management system according to claim 1, wherein
the sound data includes voice of the user,
the processor further determines whether or not an emotion of the user recognized from the voice of the user in the sound data indicates that the user has no stress, and
in response to determining that the stress level of the user exceeds the first threshold and the emotion of the user recognized from the voice of the user in the sound data indicates that the user has no stress, the processor does not notify the user of the result and does not notify the notification target person of a notification content.

11. The stress management system according to claim 1, further includes
a camera that detects, as the life log data, image data including an image of the user,
the processor determines whether or not an expression of the user recognized from the image data indicates that the user has no stress, and
in response to determining that the stress level of the user exceeds the first threshold and the expression of the user recognized from the image data indicates that the user has no stress, the processor does not notify the user of the result and does not notify the notification target person of a notification content.

12. A stress management method, comprising:
detecting, using at least one biometric sensor, a heart rate, a body temperature, a blood pressure and perspiration of a user;
detecting, using a microphone, sound data from an environment around the user;
generating stress data indicating a time series variation of a stress level of the user, the stress level being determined by summing a product of the heart rate and a first coefficient, a product of the body temperature and a second coefficient, a product of the blood pressure and a third coefficient, and a product of the perspiration and a fourth coefficient;
detecting that the stress level of the user included in the stress data exceeds a first threshold, and a time at which the stress level exceeds the first threshold;
determining whether or not stress of the user is interpersonal stress caused by contact with another person, using the sound data at the detected time, in response to detecting that the stress level of the user included in the stress data exceeds the first threshold;
in response to determining that the stress of the user is interpersonal stress, determining an assailant who is a cause of the stress by performing a voice print matching using the sound data at the detected time, and notifying, via a network, the user of a result of the determination, and notifying the assailant that an anonymous victim has the stress classified as interpersonal stress because of the assailant; and in response to determining that the stress of the user is not interpersonal stress, notifying, via the network, an outsider who is associated with the user that the user has stress other than the interpersonal stress.

13. The stress management system according to claim 1, wherein the memory stores terms in association with a type of interpersonal stress, and the processor further performs operations including:

converting the sound data into text data by performing sound recognition processing on the sound data;

determining whether or not the text data at the detected time includes a term of the terms stored in the memory; and in response to determining that the text data at the detected time includes the term of the terms stored in the memory, determining the type of stress associated with the term included in the text data as the type of stress experienced by the user at the detected time.

\* \* \* \* \*

UNITED STATES PATENT AND TRADEMARK OFFICE
CERTIFICATE OF CORRECTION

Page 1 of 1

PATENT NO.        : 10,959,657 B2
APPLICATION NO.   : 15/700315
DATED             : March 30, 2021
INVENTOR(S)       : Yuumi Kaneko et al.

It is certified that error appears in the above-identified patent and that said Letters Patent is hereby corrected as shown below:

On the Title Page

Item (30) Foreign Application Priority Data, please add:
-- September 16, 2016 (JP).........JP2016-181161 --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*